US012665068B2

(12) United States Patent
Dennis et al.

(10) Patent No.: US 12,665,068 B2
(45) Date of Patent: Jun. 23, 2026

(54) SYSTEMS AND METHODS FOR PROVIDING TREATMENT FOR PSYCHIATRIC CONDITIONS

(71) Applicants: Tracy A Dennis, New York, NY (US); Nayan B Ghosh, Brooklyn, NY (US)

(72) Inventors: Tracy A Dennis, New York, NY (US); Nayan B Ghosh, Brooklyn, NY (US)

( * ) Notice: Subject to any disclaimer, the term of this patent is extended or adjusted under 35 U.S.C. 154(b) by 0 days.

(21) Appl. No.: 18/139,780

(22) Filed: Apr. 26, 2023

(65) Prior Publication Data

US 2024/0087722 A1 Mar. 14, 2024

Related U.S. Application Data

(60) Provisional application No. 63/335,454, filed on Apr. 27, 2022.

(51) Int. Cl.
G16H 20/70 (2018.01)
A61B 5/16 (2006.01)
(Continued)

(52) U.S. Cl.
CPC .............. G16H 20/70 (2018.01); A61B 5/16 (2013.01); A63F 9/0096 (2013.01); A63F 13/47 (2014.09); A63F 13/67 (2014.09); G09B 5/02 (2013.01)

(58) Field of Classification Search
None
See application file for complete search history.

(56) References Cited

U.S. PATENT DOCUMENTS 6,485,417 B1 * 11/2002 Bowles ................ A61B 5/1101
                                                    600/300
8,602,789 B2 * 12/2013 Hallowell .............. G16H 50/30
                                                    434/167
(Continued)

OTHER PUBLICATIONS

YouTube Video "Personal Zen" https://www.youtube.com/watch?v=BmPIUVFjnEU May 24, 2019 (Year: 2019).*
(Continued)

*Primary Examiner* — Xuan M Thai
*Assistant Examiner* — Andrew Bodendorf
(74) *Attorney, Agent, or Firm* — Timothy J. Bortree

(57) ABSTRACT

Systems and methods for providing treatment for psychiatric conditions are disclosed. Preferred systems include programs stored in a memory and configured to be executed by processors to treat a subject for a psychiatric condition. The programs include instructions for conducting a therapy session, which includes a plurality of sequential turns. Each turn includes: (i) displaying, for a predetermined focal point indicator display time period and thereafter terminating the displaying of, a focal point indicator at a focal point indicator location in a display area of a display; (ii) after terminating the display of the focal point indicator, displaying, together for a predetermined stimulus display time period and thereafter terminating the display of, first and second stimulus images at respective first and second stimulus image locations in the display area, the first and second stimulus images being associated with respective first and second stimuli, the stimulus image locations being of equal prominence in relation to the focal point indicator location; (iii) after terminating the display of the stimulus images, displaying in connection with the first stimulus image location a response invitation indicator; (iv) receiving a user input in response to the display of the response invitation indicator; (v) determining at least one user input aspect of
(Continued)

the user input related to the display of the response invitation indicator; and (vi) when the at least one user input aspect has at least one desired characteristic, implementing a user incentive to modify the user input aspect for a subsequent turn.

1 Claim, 12 Drawing Sheets

(51) Int. Cl.

| | |
|---|---|
| *A63F 9/00* | (2006.01) |
| *A63F 13/47* | (2014.01) |
| *A63F 13/67* | (2014.01) |
| *G09B 5/02* | (2006.01) |

(56) References Cited

U.S. PATENT DOCUMENTS

| | | | | |
|---|---|---|---|---|
| 8,831,758 | B1* | 9/2014 | Chu | A63F 13/70 |
| | | | | 463/31 |
| 8,851,978 | B1* | 10/2014 | Koh | G07F 17/3267 |
| | | | | 463/25 |
| 9,308,446 | B1* | 4/2016 | Merzenich | A63F 13/537 |
| 9,333,421 | B2* | 5/2016 | Walls | A63F 13/20 |
| 9,387,400 | B2* | 7/2016 | Norden | A63F 13/537 |
| 9,399,111 | B1* | 7/2016 | Hanina | A61M 21/02 |
| 9,399,144 | B2* | 7/2016 | Howard | A61B 5/7282 |
| 9,754,441 | B1* | 9/2017 | Curtis | G07F 17/3209 |
| 10,085,688 | B2* | 10/2018 | Eizenman | G16H 50/20 |
| 10,311,645 | B1* | 6/2019 | Ravindran | A61B 5/163 |
| 12,161,410 | B2* | 12/2024 | Blaha | A61B 3/0091 |
| 2005/0233790 | A1* | 10/2005 | Itskov | A63F 13/812 |
| | | | | 463/2 |
| 2007/0032280 | A1* | 2/2007 | Itskov | A63F 13/10 |
| | | | | 463/7 |
| 2007/0166675 | A1* | 7/2007 | Atkins | G09B 7/04 |
| | | | | 434/236 |
| 2008/0138777 | A1* | 6/2008 | Rapoza | G09B 19/00 |
| | | | | 434/238 |

| | | | | |
|---|---|---|---|---|
| 2010/0010371 | A1* | 1/2010 | Zayfert | G16H 20/70 |
| | | | | 600/558 |
| 2011/0027765 | A1* | 2/2011 | Nader | G16H 20/70 |
| | | | | 434/236 |
| 2013/0296058 | A1* | 11/2013 | Leyland | A63F 13/245 |
| | | | | 463/42 |
| 2013/0331162 | A1* | 12/2013 | Krivicich | G06F 3/04812 |
| | | | | 463/9 |
| 2014/0106877 | A1* | 4/2014 | Knutsson | A63F 13/25 |
| | | | | 463/31 |
| 2014/0235306 | A1* | 8/2014 | Walls | A63F 13/45 |
| | | | | 463/9 |
| 2014/0349261 | A1* | 11/2014 | Dennis | G09B 5/02 |
| | | | | 434/236 |
| 2016/0155353 | A1* | 6/2016 | Merzenich | G09B 5/06 |
| | | | | 434/236 |
| 2016/0155354 | A1* | 6/2016 | Merzenich | A63F 13/47 |
| | | | | 434/236 |
| 2016/0155355 | A1* | 6/2016 | Merzenich | A63F 13/80 |
| | | | | 434/236 |
| 2017/0098385 | A1* | 4/2017 | Martucci | A61B 5/4088 |
| 2017/0148343 | A1* | 5/2017 | Merzenich | A63F 13/47 |
| 2018/0043267 | A1* | 2/2018 | Boer | A63F 13/48 |
| 2018/0286273 | A1* | 10/2018 | Kofler | G09B 19/00 |
| 2018/0304155 | A1* | 10/2018 | Pieron | G07F 17/3241 |
| 2019/0159716 | A1* | 5/2019 | Alailima | G09B 5/00 |
| 2019/0388786 | A1* | 12/2019 | D'angelo | A63F 13/537 |
| 2020/0155053 | A1* | 5/2020 | Bernstein | A61B 5/163 |
| 2020/0346115 | A1* | 11/2020 | Luo | A63F 13/5375 |
| 2023/0012960 | A1* | 1/2023 | Krishnan | A61B 5/486 |
| 2023/0136754 | A1* | 5/2023 | Asis | G16H 40/63 |
| | | | | 705/2 |
| 2023/0372829 | A1* | 11/2023 | Maggio | A63F 13/52 |

OTHER PUBLICATIONS

Tracy A. Dennis-Tiwary et al. "For whom the bell tolls: Neurocognitive individual differences in the acute stress-reduction effects of an attention bias modification game for anxiety" © 2015 Elsevier Ltd. All rights reserved. (Year: 2015).*

* cited by examiner

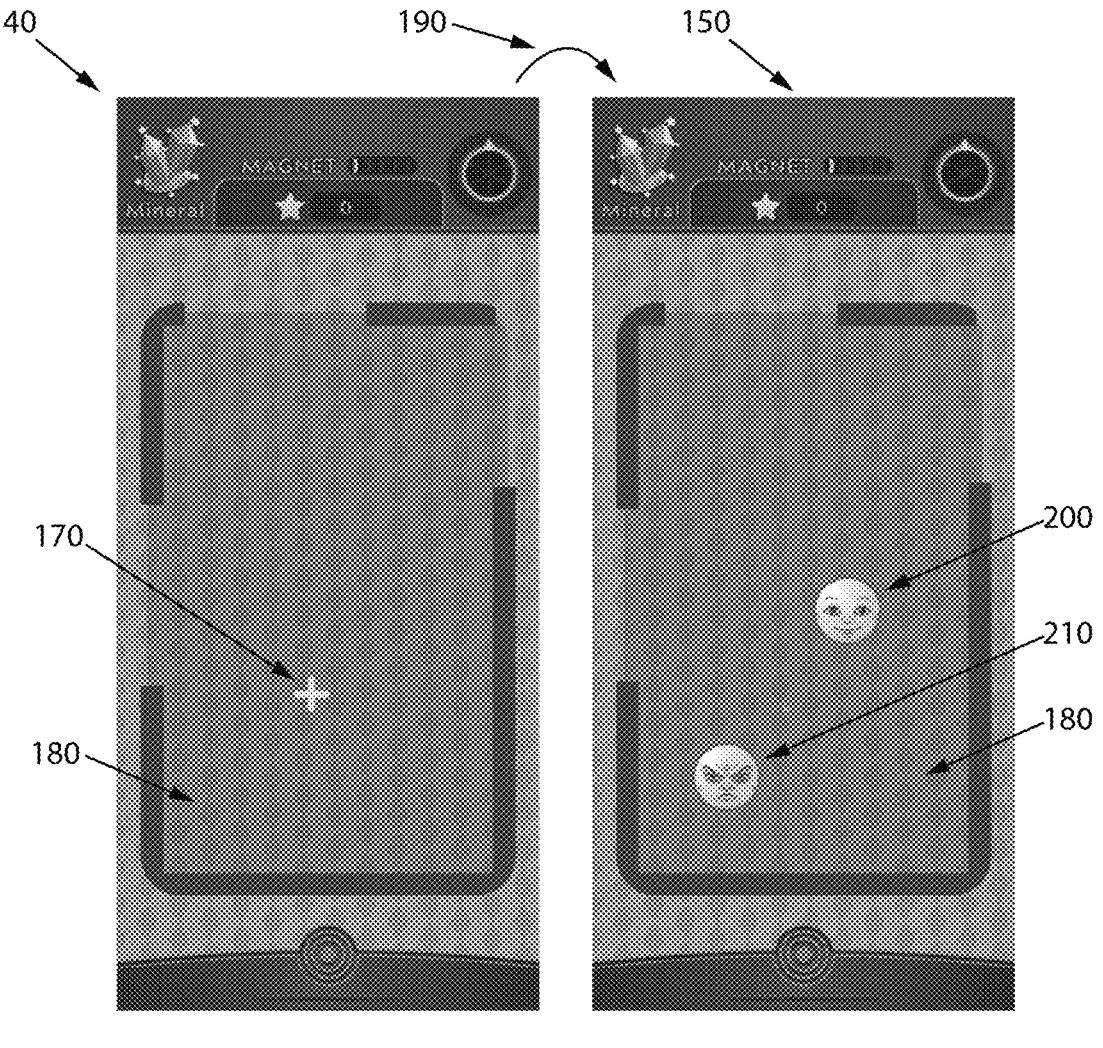
FIG. 3A                    FIG. 3B 210    200
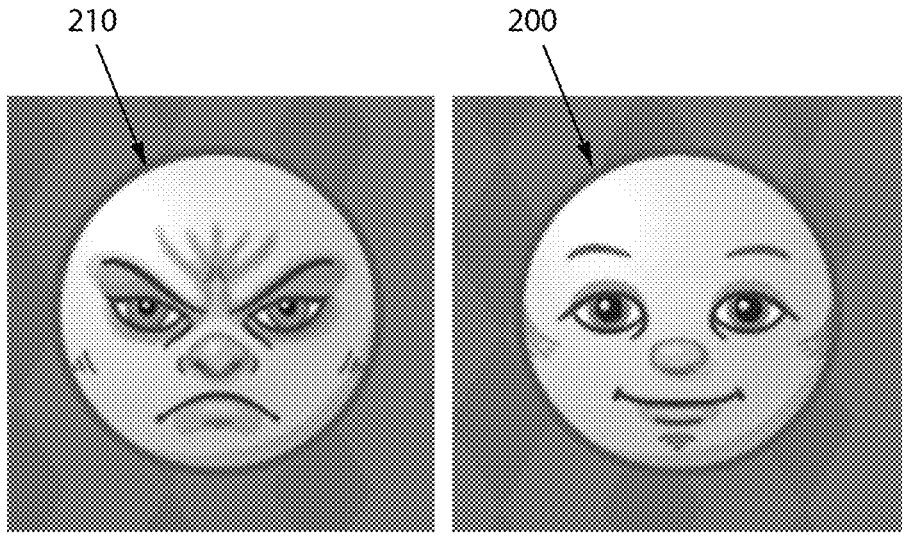
FIG. 5A                    FIG. 5B

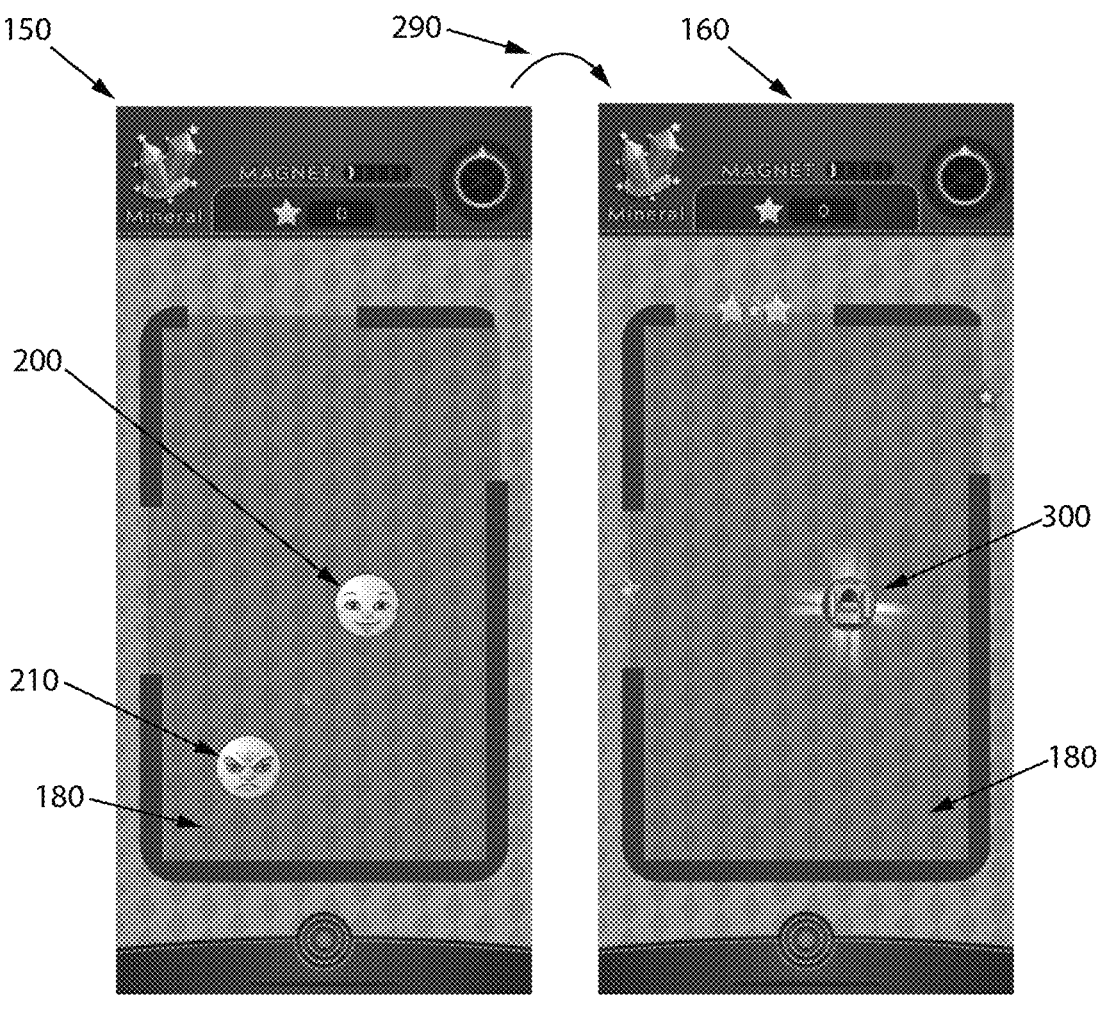
FIG. 6A                              FIG. 6B

460

480

470

490

Clinical Pilot Trial Results

The most recent clinical trial results, comparing the example embodiment to a gold-standard placebo control, are shown below.

In the active arm, more than 90% of participants showed reductions in LSAS anxiety symptoms, averaging 33%

The active arm (N=50) resulted in a mean LSAS reduction significantly above that of the control group (N=40)

68% of participants saw a clinically meaningful reduction in their anxiety severity level 38% showed reductions to sub-clinical cutoffs

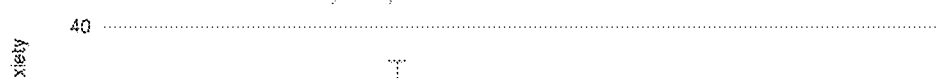

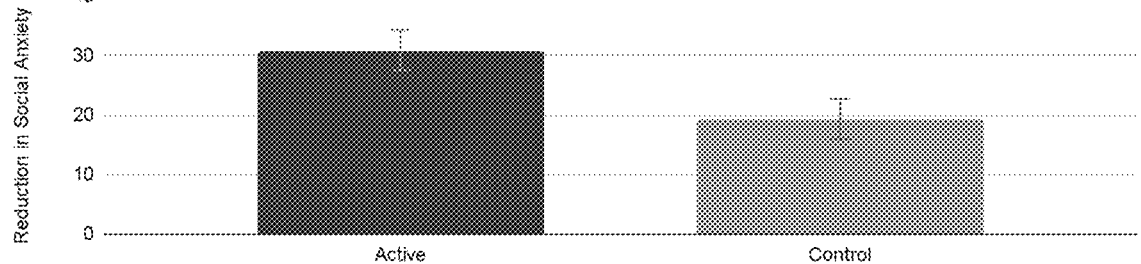

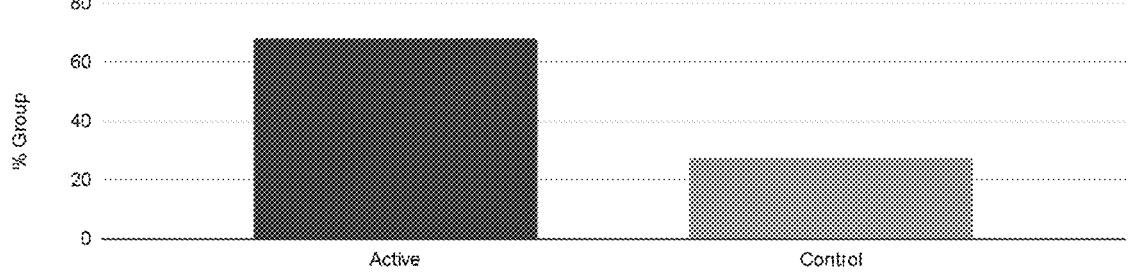

FIG. 12

SYSTEMS AND METHODS FOR PROVIDING TREATMENT FOR PSYCHIATRIC CONDITIONS

CROSS REFERENCE TO RELATED APPLICATION

The present application claims priority from U.S. Provisional Application No. 63/335,454 (filed Apr. 27, 2022), the entire disclosure of which, including but not limited to any and all cited references, is incorporated herein by reference.

FIELD OF THE INVENTION

The invention relates generally to systems and methods for providing treatment, and more specifically to systems and methods for providing treatment for psychiatric conditions.

BACKGROUND OF THE INVENTION

Millions of people worldwide have suffered or are suffering from one or more distress and fear-related disorders, including generalized anxiety disorder (GAD), social anxiety disorder (SAD), major depressive disorder (MDD), post-traumatic stress disorder (PTSD), dysthymic disorder, panic, agoraphobia, and other specific phobias (collectively, Distress and Fear-Related Disorders or DFRDs) (Watson, 2005).

DFRDs are often treated by pharmaceuticals, such as selective serotonin reuptake inhibitors (SSRIs) or benzodiazepines. However, Attention Training (AT) was developed to treat DFRDs without administration of pharmaceuticals.

AT emerged from research on anxiety-related Attention Bias (AB), a disruption in attentional processing of threat that underlies the etiology and maintenance of anxiety disorders such as GAD and SAD (Bar-Haim, Lamy, Pergamin, Bakermans Kranenburg, & van Uzendoorn, 2007; Brotman et al., 2007; Fox, Russo, Bowles, & Dutton, 2001; Fox, Russo, & Dutton, 2002; Mathews & Mackintosh, 1998; Mathews & MacLeod, 1985, 2002).

AB refers to selective and exaggerated attention towards threat. AB is thought to emerge in childhood (Puliafico & Kendall, 2006; Roy et al., 2008) and occurs automatically and unconsciously, acting as an information filter that selects threat-relevant information at the expense of signals indicating positive outcomes or safety. This cognitive bias, if sustained over time, causes a cascade of cognitive, affective, and biological changes that give rise to and maintain symptoms of anxiety (Bar-Haim et al., 2007; Dennis-Tiwary et al., 2019; MacLeod & Mathews, 1988; MacLeod, Mathews, & Tata, 1986). AB is implicated in the emergence and expression of anxiety across diagnostic categories (Bar-Haim et al., 2007) and predicts a persistent course of anxiety from childhood to adulthood (Bar-Haim et al., 2007; Perez-Edgar et al., 2010; Perez-Edgar et al., 2011).

One known form of AT uses a "dot probe" test. In a dot probe test, users are simultaneously exposed to a threatening and a non-threatening stimulus in two separate locations for approximately 500 ms. Once the threatening and non-threatening stimuli disappear, an unemotional probe is immediately displayed in one of these two separate locations and the user is required to identify the location of the probe.

In conventional dot probe testing, the probe is equally likely to be displayed in the area where the threatening stimulus was displayed as in the area where the non-threatening stimulus was displayed. A user suffering from DFRDs is expected to have a faster response for identifying the probe when the probe is positioned in the area showing the threatening stimulus due to an increased attention to the threatening image and difficulty disengaging with the threatening stimulus.

In a known variation of AT, the dot probe testing is presented wherein the probe is displayed more frequently in the area where the non-threatening stimulus was displayed. The recurring display of both threatening and non-threatening stimuli with an increase in the proportion of the dot probe appearing in the area opposite of the individual's attention bias has been shown to reduce the user's threat bias. This results in a lowering of the user's anxiety and stress.

U.S. Patent Application Publication No. US2011/0027765A1 to Nader teaches a computerized version of the dot probe test wherein the user is presented with a neutral and a negative stimulus, and the patient is prompted to interact with the system by inputting a response limited to one of two choices given to the patient. The response is intended to correlate with a previously displayed image. In certain embodiments, after display of a negative and a neutral stimulus, the letter "E" or "F" is displayed, and the user is required to then input an action identifying that letter such as by click of a mouse or typing on the keyboard.

A form of AT called Attention Bias Modification (ABM) is a computer-based treatment approach that ameliorates AB, with the downstream effect of alleviating anxiety-related symptoms (Beard, Sawyer, & Hofmann, 2012; Hakamata et al., 2010; Hallion & Ruscio, 2011; MacLeod, Rutherford, Campbell, Ebsworthy, & Holker, 2002; Mogoae, David, & Koster, 2014). ABM has been particularly successful in the treatment of GAD and SAD (e.g., Amir, Beard, Burns, & Bomyea, 2009; Amir, Beard, Taylor, et al., 2009; Klumpp & Amir, 2010), showing reductions of clinical symptoms comparable to treatment effect sizes of traditional Cognitive Behavioral Therapy (CBT).

However, current computerized versions of AT have significant drawbacks. Prominent among those is that their effectiveness depends on the consistent and lengthy participation in the testing by the subject, and to date, implementations of the dot probe test have failed to maintain the focused attention of even the most dedicated subjects.

Accordingly, there is a need for systems and methods for providing treatment for psychiatric conditions, including but not limited to DFRDs, that keep subjects consistently engaged in meaningful participation for the extended periods of time necessary to provide effective results.

SUMMARY OF THE INVENTION

The invention advantageously fills the aforementioned deficiencies by providing systems and methods for conducting therapy for the treatment of psychiatric conditions.

The following descriptions of features and aspects of the invention are not meant to limit the scope of the invention, but rather to merely provide examples of preferred embodiments. Terms and phrases used are intended to have and convey their dictionary and common usage meanings, as well as or including, without limitation, the meanings specified. Terms and phrases used to convey direction or position, whether relative or absolute, are merely examples and do not limit the invention to only those directional or positional terms and phrases used, but rather the invention encompasses embodiments having components or features that are directed or positioned differently. To the extent that any refer to functionality or purpose in any way, they are intended to convey, in addition to their dictionary and common usage meanings, any arrangement, combination, or interaction of physical objects, hardware, and/or software that is suitable to any degree, whether partially or fully, for accomplishing and/or effecting the function or intended result. Further, in addition to any preferred embodiments described, the invention encompasses embodiments having features and aspects that fall into the broadest possible categories to which the described preferred features and aspects belong.

The present invention provides, in preferred embodiments, a system and method for providing treatment for psychiatric conditions.

In an example embodiment, the present invention is implemented by way of a mobile application for treating anxiety disorders. Use of the mobile application for treating anxiety disorders involves the repetition of a simple, swipe-based user interaction during each turn of a plurality of treatment sessions. Each turn's user interaction trains the user to attend away from an unpleasant (e.g., a threatening) Facial Stimuli and instead attend toward a pleasant (e.g., a non-threatening) Facial Stimuli.

The present invention is useful for treating a subject in need of treatment of a psychiatric condition. Psychiatric conditions that can be treated using one or more embodiments of the present invention include but are not limited to DFRDs.

The course of treatment preferably includes at least one therapy session, and preferably a plurality of therapy sessions, with each therapy session preferably including at least one turn, and preferably a plurality of sequential turns.

Each turn of a treatment session preferably includes one or more of the following steps/functions:

(i) displaying, for a predetermined focal point indicator display time period and thereafter terminating the displaying of, a focal point indicator (e.g., a Fixation Point) at a focal point indicator location in a display area of a display (e.g., a touch screen of a smartphone);

(ii) after terminating the display of the focal point indicator, displaying, together for a predetermined stimulus display time period and thereafter terminating the display of, first and second stimulus images (e.g., non-threatening and threatening Facial Stimuli) at respective first and second stimulus image locations in the display area of the display, the first and second stimulus images being associated with respective first and second stimuli, the first and second stimulus image locations being of equal prominence in relation to the focal point indicator location (e.g., at locations equidistant from the location at which the Fixation Point had been displayed);

(iii) after terminating the display of the first and second stimulus images, displaying in connection with the first stimulus image location a response invitation indicator (e.g., a spaceship or ball);

(iv) receiving a user input (e.g., a swiping touch input) in response to the display of the response invitation indicator;

(v) determining at least one user input aspect of the user input related to the display of the response invitation indicator (e.g., a Reaction Time, which is a time period between when the spaceship was displayed and the user touched the touch screen at the location of the spaceship); and (vi) when the at least one user input aspect has at least one desired characteristic (e.g., when the Reaction Time is shorter than a Reaction Time Threshold), implementing a user incentive to modify the user input aspect for a subsequent turn (e.g., changing the Reaction Time Threshold for the next turn).

In preferred embodiments, these steps/functions are experienced by the user in three stages: a first stage (e.g., a Fixation Stage), in which a focal point indicator (e.g., Fixation Point) is displayed; a second stage (e.g., a Facial Stimuli Stage), in which first and second stimulus images (e.g., non-threatening and threatening Facial Stimuli) are displayed; and a third stage (e.g., a Gameplay Stage), in which a response invitation indicator (e.g., a Gameplay Stimulus) is displayed and user input (e.g., a swiping touch input) is received in response to the display of the response invitation indicator.

Preferably, with regard to determining at least one user input aspect of the user input related to the display of the response invitation indicator, and, when the at least one user input aspect has at least one desired characteristic, implementing a user incentive to modify the user input aspect for a subsequent turn, the incentive is configured to (1) effect the mechanism of action that treats the condition, and/or (2) encourage continued user participation in one or more treatment sessions.

Preferably, with regard to the user incentive effecting a mechanism of action that treats the condition, the mechanism of action includes one or more of (1) training the user to reduce an input time period and (2) rewarding the user for reducing the input time period, wherein the input time period is a time period between the display of the response invitation indicator and the receiving of the user input.

Preferably, with regard to the mechanism of action including training the user to reduce an input time period, training the user to reduce the input time period includes comparing the input time period to an incentive time period and, when the input time period is related to the incentive time period in accordance with a predetermined formula, decreasing the incentive time period for a subsequent turn. Preferably, when the input time period is less than the incentive time period, the incentive time period is decreased for a subsequent turn.

Preferably, with regard to the mechanism of action including rewarding the user for reducing the input time period, rewarding the user for reducing the input time period includes comparing the input time period to an incentive time period, and, when the input time period is related to the incentive time period in accordance with a predetermined formula, awarding the user one or more of (1) one or more rewards and (2) an opportunity to obtain one or more rewards.

Preferably, with regard to the user incentive encouraging continued user participation in one or more treatment sessions, the user incentive encourages user participation in one or more subsequent treatment sessions, and most preferably encourages user participation from one treatment session to another treatment session.

The invention now will be described more fully hereinafter with reference to the accompanying drawings, which are intended to be viewed in conjunction with both this summary, the detailed description, and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough and complete and will fully convey the full scope of the invention to those skilled in the art.

BRIEF DESCRIPTION OF THE DRAWINGS

FIGS. 3A and 3B illustrate, respectively, first and second stages of a turn of a treatment session of the example embodiment of the present invention.

FIGS. 5A and 5B illustrate, respectively, unpleasant (e.g., threatening) and pleasant (e.g., non-threatening) facial stimuli of the example embodiment of the present invention.

FIGS. 6A and 6B illustrate, respectively, second and third stages of a turn of a treatment session of the example embodiment of the present invention.

FIG. 12 illustrates results of a clinical trial of an embodiment of the present invention.

DETAILED DESCRIPTION OF PREFERRED EMBODIMENTS

Figure 1:
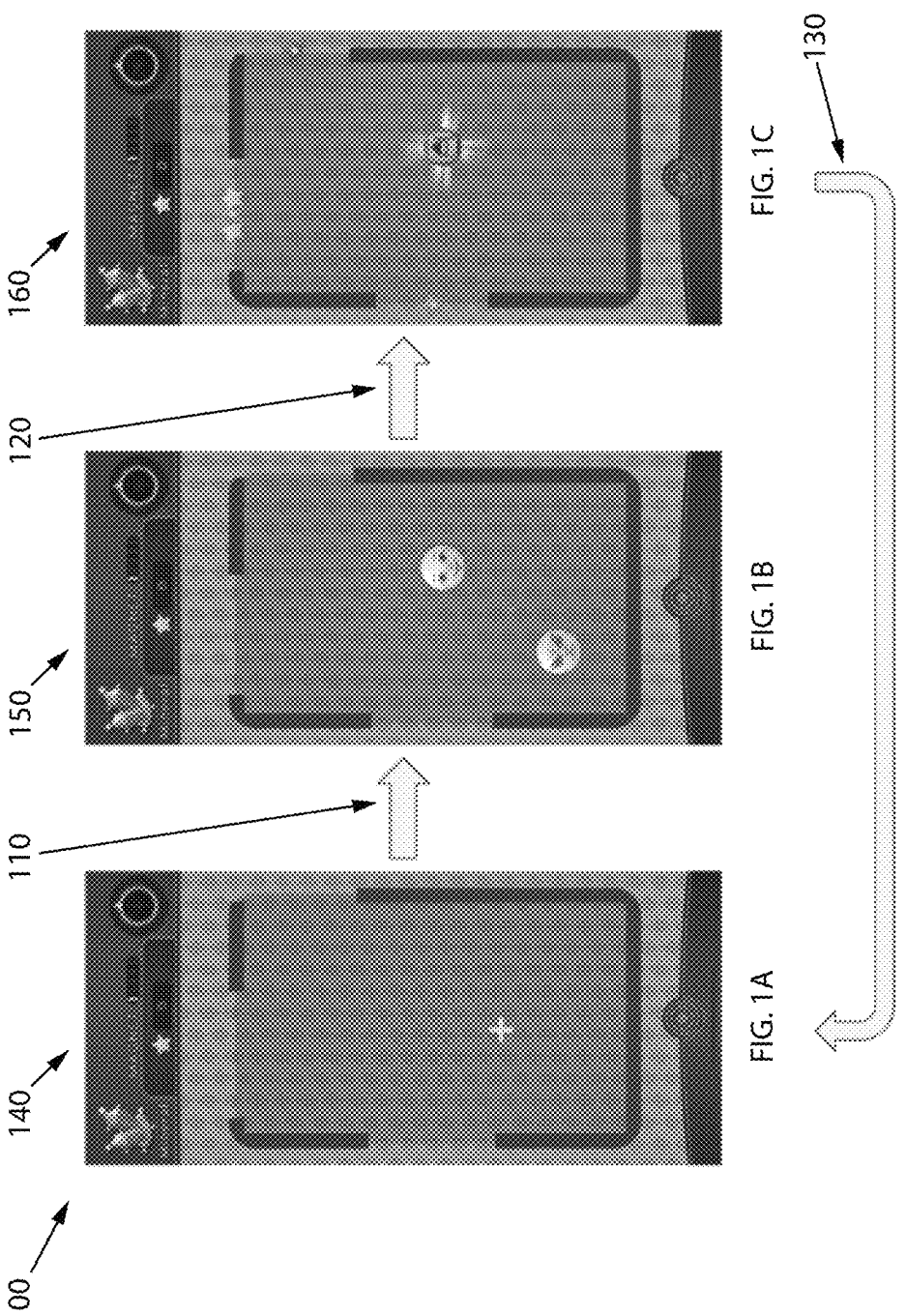
FIGS. 1A, 1B and 1C illustrate a treatment session of an example embodiment of the present invention.

1. Broad Scope and Non-Limitation of Described Embodiments

Following are more detailed descriptions of various concepts related to, and embodiments of, apparatus and methods according to the present disclosure. Various aspects of the subject matter introduced above and discussed in greater detail below may be implemented in any of numerous ways, as the subject matter is not limited to any particular manner of implementation. Examples of specific implementations and applications are provided primarily for illustrative purposes. Headings used herein are primarily for organizational purposes and do not limit the scope of the present invention.

The present invention encompasses any and all described components, elements, steps and representations, whether as or part of systems, apparatus, devices, methods, computer programs, data structures, recording mediums, and the like, and any and all combinations, permutations, and conversions between thereof. Any one or more functions that are illustrated and/or described may be implemented only in hardware, only in software, or in a combination of hardware and software, and are not limited to being implemented in only one or the other.

2. Overview

The present invention provides, in preferred embodiments, a system and method for providing treatment for psychiatric conditions.

The present invention is useful for treating a subject in need of treatment of a psychiatric condition. Psychiatric conditions that can be treated using one or more embodiments of the present invention include but are not limited to DFRDs. It should be understood that one or more embodiments of the present invention can be used to treat one or more subjects, each with the same psychiatric condition. It should be understood that one or more embodiments of the present invention can be used to treat one or more subjects, each with a different psychiatric condition.

The course of treatment preferably includes at least one therapy session, and preferably a plurality of therapy sessions, with each therapy session preferably including at least one turn, and preferably a plurality of sequential turns.

2.1. Example Aspects of the Invention

In an aspect, the present invention is directed to a computing system that includes one or more processors, memory, and one or more programs. The one or more programs are stored in the memory and are configured to be executed by the one or more processors to treat a subject in need of treatment of a psychiatric condition. The one or more programs include instructions for providing a therapy session, the therapy session includes a plurality of sequential turns, and each turn includes one or more of the steps and/or functions discussed below.

In another aspect, the present invention is directed to a non-transitory, computer readable storage medium that contains a program, which when executed by a computer, causes the computer to provide a therapy session comprising a plurality of sequential turns by carrying out actions for each turn, including one or more of the steps and/or functions discussed below.

In yet another aspect, the present invention is directed to a method of providing a therapy session, the therapy session includes a plurality of sequential turns, and each turn includes one or more of the steps and/or functions discussed below.

2.2. Steps/Functions of Each Turn

Each turn of a treatment session preferably includes one or more of the following steps/functions:

(i) displaying, for a predetermined focal point indicator display time period and thereafter terminating the displaying of, a focal point indicator at a focal point indicator location in a display area of a display;

(ii) after terminating the display of the focal point indicator, displaying, together for a predetermined stimulus display time period and thereafter terminating the display of, first and second stimulus images at respective first and second stimulus image locations in the display area of the display, the first and second stimulus images being associated with respective first and second stimuli, the first and second stimulus image locations being of equal prominence in relation to the focal point indicator location;

(iii) after terminating the display of the first and second stimulus images, displaying in connection with the first stimulus image location a response invitation indicator;

(iv) receiving a user input in response to the display of the response invitation indicator;

(v) determining at least one user input aspect of the user input related to the display of the response invitation indicator; and (vi) when the at least one user input aspect has at least one desired characteristic, implementing a user incentive to modify the user input aspect for a subsequent turn.

2.3. Descriptions in Context of an Example Embodiment

Preferred aspects of these steps/functions will be described below, along with descriptions of an example embodiment of the present invention in which one or more are implemented.

3. Introduction of the Example Embodiment

In an example embodiment that will be discussed in detail herein, a system and method for providing treatment for psychiatric conditions is implemented by way of a mobile application for treating anxiety disorders. Use of the mobile application for treating anxiety disorders involves the repetition of a simple, swipe-based user interaction during each turn of a plurality of treatment sessions. Each turn's user interaction trains the user to attend away from an unpleasant (e.g., a threatening) Facial Stimuli and instead attend toward a pleasant (e.g., a non-threatening) Facial Stimuli.

3.1. Treatment, Sessions and Turns

According to the present invention, a course of treatment can include one or more treatment sessions, and preferably includes between 12 and 16 sessions, and most preferably 16 sessions. Each session can include one or more turns, and preferably includes between 100 and 250 turns, more preferably between 120 and 200 turns, and most preferably 180 turns. Preferably, each session is completed during a single day. Preferably, over a period of one month, the number of turns engaged in by a user is inclusively between 1,000 and 4,000, and most preferably between 1,200 and 3,000 turns. In certain embodiments, the number of turns is a predetermined number (e.g., determined prior to the start of treatment, or determined prior to the start of a session, or prior to the start of a turn). In some embodiments, the number of turns is determined during a treatment session (e.g., based on the at least one user input aspect of the user input). For example, if a user is progressing quickly through the course of treatment and/or if a user adheres closely to a treatment schedule, the number of turns in each session may be decreased from an initial predetermined number. Conversely, for example, if a user is progressing slowly through the course of treatment and/or if a user adheres loosely to a treatment schedule, the number of turns in each session may be increased from an initial predetermined number. As another example, the number of turns can be determined during a treatment session based on user input related to reporting user levels of stress, fatigue, pain and/or other user characteristics or concerns.

In preferred embodiments, dosage (e.g., the extent to which the treatment should be utilized) is determined by "number of turns" rather than time duration. This can ensure standardization of dosage, because variability in user performance and reaction times can impact the time needed to advance through the treatment.

In the example embodiment, a course of treatment includes 16 sessions, and each session includes a predetermined number of 180 turns. Preferably, a single session consists of 180 turns, averaging 11:36 minutes with a 95% confidence interval of [11:32, 11:40]. Study data and usability testing data indicate that deviation from average sessions times is minimal

3.2. Turn Stages

According to the present invention, each turn of a session preferably includes one or more of the steps/functions (i) through (vi) listed above.

In preferred embodiments, these steps/functions are experienced by the user in three stages: a first stage, in which a focal point indicator is displayed; a second stage, in which first and second stimulus images are displayed; and a third stage, in which a response invitation indicator is displayed and user input is received in response to the display of the response invitation indicator.

Reference is now made to FIGS. 1A, 1B and 1C, which illustrate a flowchart of a treatment session of the example embodiment. Each figure depicts a screenshot of the mobile application of the example embodiment.

In the example embodiment, a treatment session 100 of the embodiment includes 180 turns. Each turn includes three stages. The first stage 140, depicted in the screenshot of FIG. 1A, is referred to as a Fixation Stage. The second stage 150, depicted in the screenshot of FIG. 1B, is referred to as a Facial Stimuli Stage, which follows the Fixation Stage (as indicated by arrow 110). The third stage 160, depicted in the screenshot of FIG. 1C, is referred to as a Gameplay Stage, which follows the Facial Stimuli Stage (as indicated by arrow 120). After the Gameplay Stage, a new turn begins with a subsequent Fixation Stage (as indicated by arrow 130). These stages will be discussed in greater detail below.

3.2.1. First Stage (Fixation Stage)

In preferred embodiments, a purpose of the first stage is to draw the user's attention to a focal point indicator. As will be discussed further in connection with the second stage, drawing the user's attention to the focal point indicator preferably (1) provides the user with an advance indication as to where the first and second stimulus images will be displayed during the second stage, and/or (2) standardizes the user's area of focus to be weighted equally in relation to the first and second stimulus images that will be displayed during the second stage. Providing the user with the advance indication can help enable the user (e.g., improve the user's ability) to reduce the input time period (discussed in greater detail below) by focusing on the focal point indicator. Standardizing the user's area of focus to be weighted equally in relation to the first and second stimulus images can be important, because the stimulus images compete for the user's attention (this approach has been validated through eye-tracking studies).

Preferably, drawing the user's attention to a focal point indicator is accomplished in the first stage by displaying the focal point indicator and then terminating the display of the focal point indicator after a focal point indicator display time period has passed. Preferably, the focal point indicator is displayed within a field visible to the user. Preferably, the location at which the focal point indicator is displayed within the field is randomized for each turn. Preferably, the focal point indicator is any image that is noticeable to the user, and most preferably is an image that draws the user's attention. Preferably, the focal point indicator is or includes one or more of the following images: a plus symbol (e.g., a "+"), an asterisk (e.g., a "*"), a hashtag (e.g., a "#"), an asperand (e.g., a "@"), an image of a target, and an icon (including but not limited to an icon relevant to a gameplay narrative). Preferably, the focal point indicator display time period is inclusively between 250 ms and 750 ms, and most preferably is 500 ms.

Figure 2:
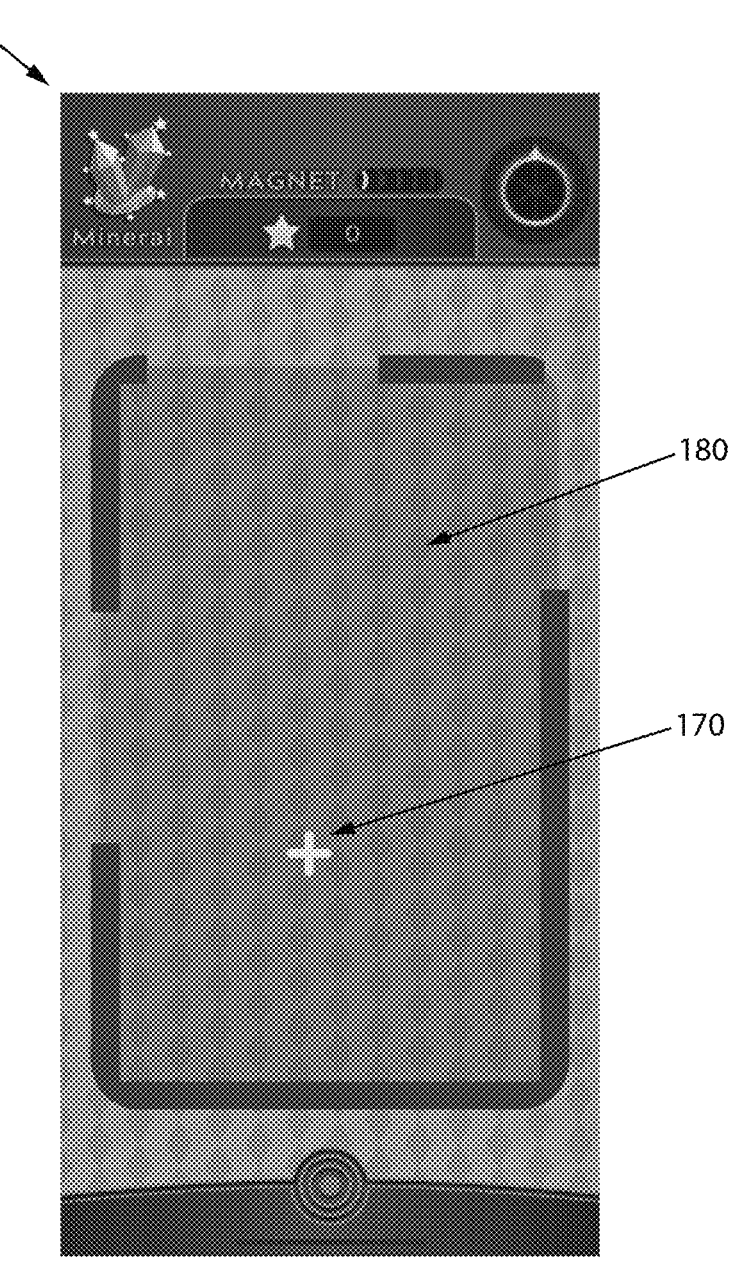
FIG. 2 illustrates a first stage of a turn of a treatment session of the example embodiment of the present invention.

Reference is now made to FIG. 2, which illustrates a first stage of a turn of a treatment session of the example embodiment.

In the example embodiment, in the Fixation Stage 140, the focal point indicator 170 (referred to in the example embodiment as a Fixation Point) is a plus symbol (e.g., a "+"). The Fixation Point 170 appears at a randomized location within a fixed rectangular field 180 on the screen of a smartphone on which the mobile application is running. The display of the Fixation Point 170 is terminated after 500 ms. The location of the Fixation Point 170 is randomized at each turn according to the following formula (referred to herein as Formula 1):

$$\text{Fixation point location} = \text{Random}(x, y)$$

Where (x, y) are located within the play area field (e.g., board); and

Where x1 is the board's lowest x-value, and x2 is the board's highest x-value; and Where y1 is the board's lowest y-value, and y2 is the board's highest y-value; and Where distance(Facial Stimulus, x1)>15%*board x-length; and Where distance(Facial Stimulus, x2)>15%*board x-length; and Where distance(Facial Stimulus, y1)>15%*board y-length; and Where distance(Facial Stimulus, y2)>15%*board y-length.

3.2.2. Second Stage (Facial Stimuli Stage)

In preferred embodiments, a purpose of the second stage is to present two different archetypal signals that the user is preferably predisposed to mentally process quickly. The archetypal signals preferably compete for the user's attention, and accordingly are preferably presented in equally prominent relation to the focal point indicator.

Preferably, presenting the archetypal signals is accomplished in the second stage by displaying first and second stimulus images and then terminating the display of the first and second stimulus images after a stimulus display time period has passed. Preferably, the stimulus display time period is inclusively between 500 ms and 1 second, and most preferably is 500 ms.

Preferably, the first and second stimulus images are associated with respective first and second stimuli. Preferably, the first and second stimulus images are configured to induce human amygdala activation. Preferably, the first and second stimulus images are associated with respective first and second emotional states. In certain preferred embodiments, the first stimulus image is associated with a non-threatening emotional state and the second stimulus image is associated with a threatening emotional state. In some of those certain and other preferred embodiments, the first stimulus image depicts a non-threatening facial expression and the second stimulus image depicts a threatening facial expression. In some of those certain and other preferred embodiments, the first stimulus image depicts a pleasant facial expression and the second stimulus image depicts an unpleasant facial expression. In some of those certain and other preferred embodiments, the first stimulus image depicts a happy facial expression and the second stimulus image depicts a sad facial expression.

For example, preferably, when the psychiatric condition being treated is an anxiety disorder and non-threatening and threatening stimuli are being used in the first and second stimulus images, it can be important that the pleasant (e.g., non-threatening) stimuli show neutral or mild expressions of happiness and contentedness (e.g., slight smiling, lifted eyebrows, etc.) and the unpleasant (e.g., threatening) stimuli show exaggerated features of unhappiness and anger (e.g., furrowed brow, frowning face, etc.).

Preferably, the first and second stimulus images are displayed within the same field in which the focal point indicator was displayed, at respective first and second stimulus image locations. Preferably, the first and second stimulus images are displayed immediately or as soon as possible following the termination of the display of the focal point indicator.

Preferably, the first and second stimulus image locations are of equal prominence in relation to the focal point indicator location. In certain preferred embodiments, the first and second stimulus image locations are equidistant from the focal point indicator location. In some of those certain and other preferred embodiments, a distance between the first and second stimulus image locations is randomized at each turn. In some of those certain and other preferred embodiments, the first and second stimulus image locations are aligned with one another and the focal point indicator location. In some of those and other preferred embodiments, an angle of the alignment is randomized at each turn.

While the present invention is described herein primarily with reference to two stimulus images, certain embodiments of the present invention may include three or more stimulus images, and the invention is not limited to the use of two stimulus images.

While the present invention is described herein primarily with reference to stimulus images that each present an image that does not change during the turn (e.g., while being displayed), session (e.g., from one turn to another) or treatment, certain embodiments of the present invention may include one or more stimulus images that change during the turn (e.g., while being displayed), session (e.g., from one turn to another) or treatment, and the invention is not limited to the use of stimulus images that each present an image that does not change. In certain embodiments, the stimulus images each present an image that changes from an initial image to a subsequent image. In some of those embodiments, the subsequent image is the initial image of another stimulus image.

Reference is now made to FIGS. 3A and 3B, which illustrate, respectively, first and second stages of a turn of a treatment session of the example embodiment. Arrow 190 indicates a screen change or screen image progression from FIG. 3A to FIG. 3B.

Figures 4A, 4B:
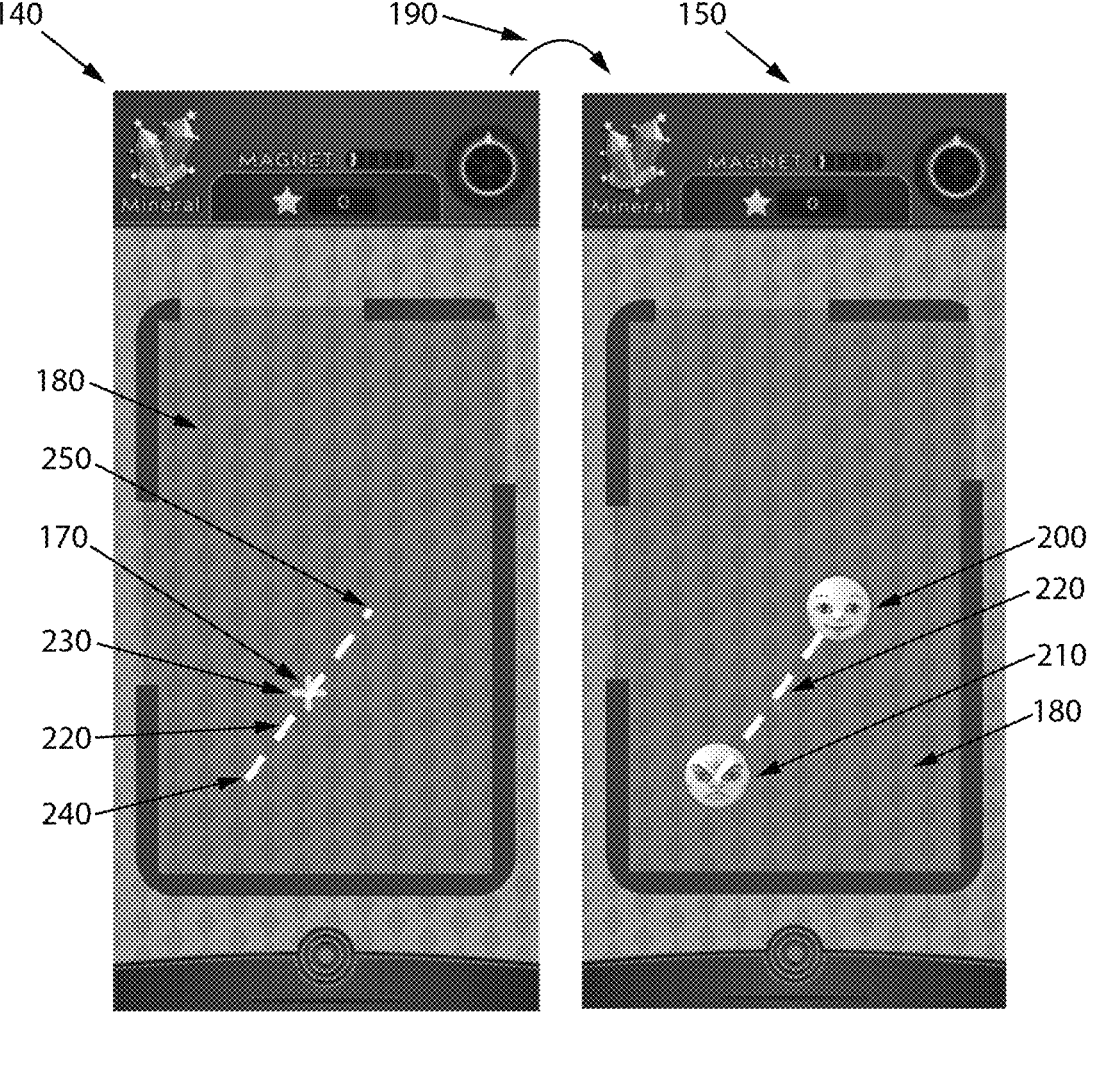
FIGS. 4A and 4B illustrate, respectively, first and second stages of a turn of a treatment session of the example embodiment of the present invention.

Reference is now made to FIGS. 4A and 4B, which illustrate, respectively, first and second stages of a turn of a treatment session of the example embodiment. Arrow 190 indicates a screen change or screen image progression from FIG. 4A to FIG. 4B.

Reference is now made to FIGS. 5A and 5B, which illustrate, respectively, threatening and non-threatening facial stimuli of the example embodiment.

In the example embodiment, in the Facial Stimuli Stage 150, the first and second stimulus images (referred to in the example embodiment as Facial Stimuli) include a first Facial Stimulus 200 that is a non-threatening facial stimulus configured as a face showing a slight smile, relaxed nose, contended eyes, and raised eyebrows, and a second Facial Stimulus 210 that is a threatening facial stimulus configured as a face showing an exaggerated frown, crinkled nose, angry eyes, and furrowed eyebrows. These Facial Stimuli 200,210 have been validated as effective through at least one clinical trial (see results illustrated in FIG. 12). In the example embodiment, the Facial Stimuli 200,210 appear within the fixed rectangular field 180 on the screen of the smartphone on which the mobile application is running, immediately or soon after the termination of the display of the Fixation Point 170, and appear at opposite ends 240,250 of a calculated line 220 having a midpoint 230 that is the location of the Fixation Point 170 determined in the first stage 140 of the turn, and a length that is randomized at each turn according to the following formula (referred to herein as Formula 2):

$$s=L/m$$

let startRot=RandomRotation( )

let angleRange=maxRange*Random(0.0,1.0)

for($r=s;r<L;r+=s$){ addedRot=Sin($r$/(($r$*0.15)+1)*angleRange;

nextRotation=startRot+addedRot nextPosition=PolarToCartesian($r$,nextRotation)

Where:
startRot=Starting rotation
angleRange=How far in radians the line oscillates
$r$=radius
$m$=minimum space between medallions (e.g., stimulus images)
L=line length
PolarToCartesian( )=function that takes polar notation values (radius and angle) and converts them to cartesian 3.2.3. Third Stage (Gameplay Stage)

In preferred embodiments, a purpose of the third stage is to incentivize the user to participate in the treatment, as to both effecting the mechanism of action that treats the condition, and encouraging continued user participation in one or more treatment sessions.

Preferably, incentivizing the user to participate in the treatment is accomplished in the third stage by displaying, in connection with the first stimulus image location, a response invitation indicator; receiving a user input in response to the display of the response invitation indicator; determining at least one user input aspect of the user input related to the display of the response invitation indicator; and when the at least one user input aspect has at least one desired characteristic, implementing a user incentive to modify the user input aspect for a subsequent turn.

3.2.3.1. Response Invitation Indicator Display

Preferably, with regard to displaying, in connection with the first stimulus image location, a response invitation indicator, the response invitation indicator depicts an image that invites interaction by the user, such as for example without limitation, a spaceship, a ball, an image of a target, and an icon (including but not limited to an icon relevant to a gameplay narrative). In certain embodiments, the response invitation indicator is associated with one or more emotional states. For example, the response invitation indicator can be one or more faces. In some of these embodiments, the one or more faces are static until a user response is received in connection with them. In other of these embodiments, the one or more faces dynamically change until a user response is received in connection with them. In certain embodiments, the response invitation indicator is associated with one or more emotional states (e.g., is one ore more faces) and the user response includes choosing between or among the one or more emotional states (e.g., is one or more faces).

Preferably, the response invitation indicator is displayed within the same field in which the focal point indicator and first and second stimulus images were displayed, at a response invitation indicator location. Preferably, the response invitation indicator is displayed immediately or as soon as possible following the termination of the display of the first and second stimulus images. Preferably, the response invitation indicator location is the location at which the first stimulus image was displayed.

Reference is now made to FIGS. 6A and 6B, which illustrate, respectively, second and third stages of a turn of a treatment session of the example embodiment. Arrow 290 indicates a screen change or screen image progression from FIG. 6A to FIG. 6B.

In the example embodiment, the response invitation indicator (referred to in the example embodiment as a Gameplay Stimulus) depicts a spaceship 300. The spaceship 300 appears within the fixed rectangular field 180 on the screen of the smartphone on which the mobile application is running, immediately or soon after the termination of the display of the Facial Stimuli 200,210, and appears at the location at which the first Facial Stimulus 200 (in this example embodiment, the non-threatening facial stimulus) had been displayed.

In some other embodiments, the spaceship appears at the location at which the threatening facial stimulus had been displayed. In yet other embodiments, the spaceship appears either at the location at which the threatening facial stimulus had been displayed, or at the location at which the threatening facial stimulus had been displayed, and the decision is randomized for each turn and/or from turn to turn. For example, in such embodiments, the randomization can be determined by the following formula (referred to herein as Formula 3):

WHILE $n>0,C(A18000-n)$, where $C(Ai)$=Choose, without replacement, from a set of $i$ objects, and where $n$=number of turns since the start of the round of turns (e.g., the session), and where $A18000$ is an array of 950 pleasant (e.g., non-threatening) Facial Stimuli and 950 unpleasant (e.g., threatening)Facial Stimuli starting points.

3.2.3.2. User Response to Response Invitation Indicator Display

Preferably, with regard to receiving a user input in response to the display of the response invitation indicator, the type of user input that is solicited facilitates an accurate user response time. For example, preferably, the mechanism of response requires minimal effort on the part of the user and/or minimizes delayed recordation of a response by the user after the effort is made. Stated alternatively, for example, goals of the mechanism of response include providing an easy method of response for the user, and/or being able to record the response as soon as possible after the user has responded.

Preferably, the type of user input that is solicited indicates a connection to the response invitation indicator. For example, preferably, the mechanism of response facilitates a direct association with the response invitation indicator. Stated alternatively, for example, a goal of the mechanism of response is to be clearly directed to the response invitation indicator.

Preferred mechanisms of response include but are not limited to touch screen touch input, physical button input, virtual button input, gesture-based input, audio input, and voice recognition input, and most preferably to the extent such mechanisms of response can indicate clear association with the response invitation indicator.

In the example embodiment, the screen of the smartphone on which the mobile application is running is a touch screen, and the mechanism of response is a touch input on the touch screen at the location of the response invitation indicator 300. For example, this mechanism of response is directed to the above-described goals inasmuch as it requires minimal effort on the part of the user, enables near instantaneous recording of the response, and indicates intent toward the response invitation indicator.

3.2.3.3. Evaluation of User Response and Incentive Implementation

Preferably, with regard to determining at least one user input aspect of the user input related to the display of the response invitation indicator, and, when the at least one user input aspect has at least one desired characteristic, implementing a user incentive to modify the user input aspect for a subsequent turn, the incentive is configured to (1) effect the mechanism of action that treats the condition, and/or (2) encourage continued user participation in one or more treatment sessions.

Figures 7A, 7B, 7C:
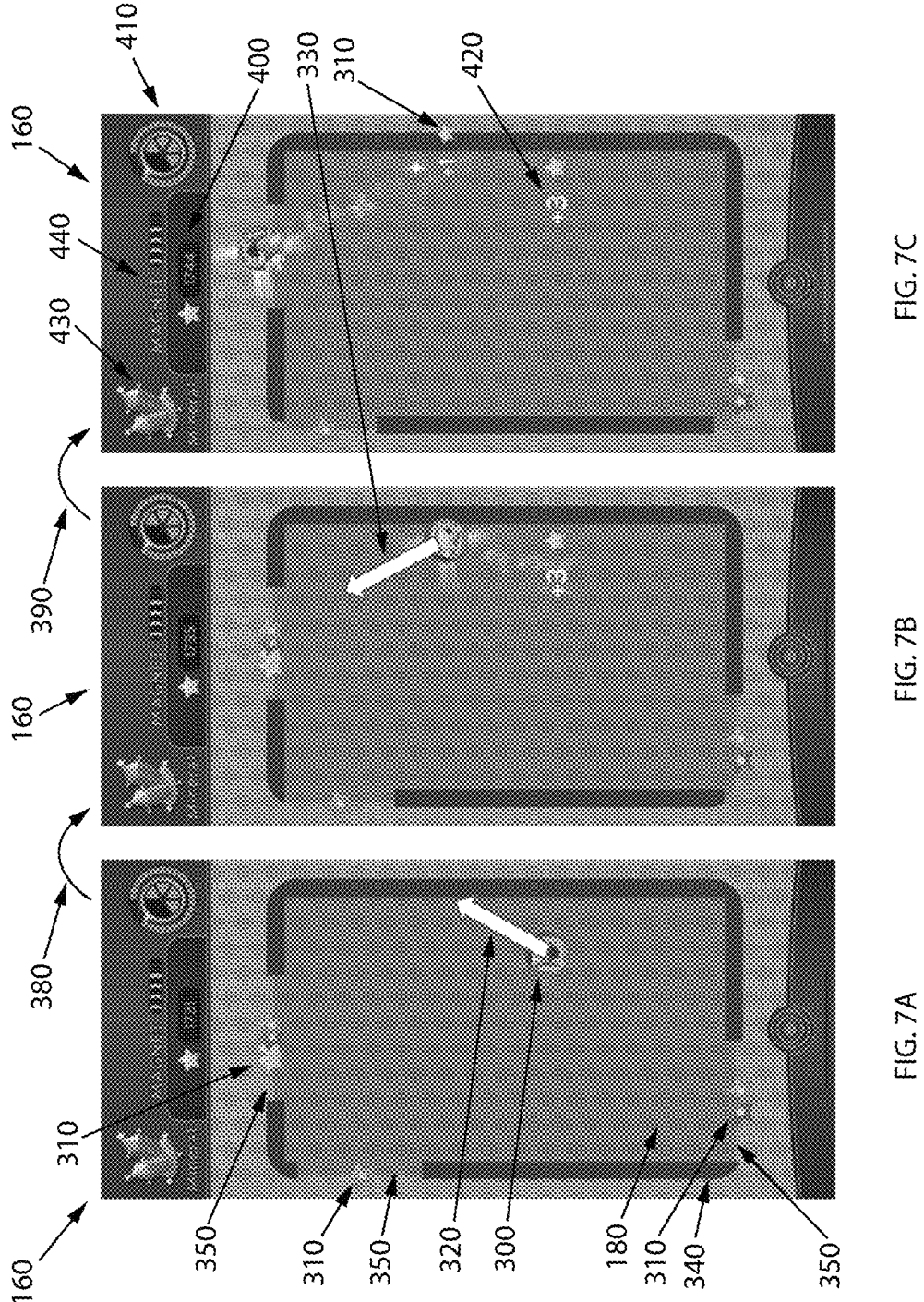
FIGS. 7A, 7B and 7C illustrate star collection during a turn of a treatment session of the example embodiment of the present invention.

Reference is now made to FIGS. 7A, 7B and 7C, which illustrate star collection during a turn of a treatment session of the example embodiment. Arrow 380 indicates a screen change or screen image progression from FIG. 7A to FIG. 7B. Arrow 390 indicates a screen change or screen image progression from FIG. 7B to FIG. 7C.

In the example embodiment, user objectives in the Gameplay Stage 160 include quickly responding to the display of the spaceship 300 and responding in such a way as to cause the spaceship 300 to collect stars 310 before the turn ends. In the example embodiment, the user can quickly respond to the display of the spaceship 300 by performing a swiping touch input at the location of the spaceship 300, and stars 300 can be collected by the user responding with a swipe that directs the spaceship 300 to engage with one or more targets that reward stars (e.g., a direction of the swipe is depicted by an arrow 320 in FIG. 7A, and movement of the spaceship 300 after bouncing off a wall 340 and encountering stars 310 is depicted by an arrow 330 in FIG. 7B). In the example embodiment, stars can be collected by the spaceship 300 doing one or more of the following: encountering stars directly (e.g., for stars that are located in the field, e.g., between the spaceship and the wall), being awarded stars for bouncing off one or more walls, and encountering stars when entering a gap in the wall (e.g., if the gap contains stars). The direction of the swipe touch input can direct the spaceship toward targets the user wants to engage for the collection of stars. In the action depicted in FIGS. 7A, 7B and 7C, the spaceship 300 has been directed to bounce off a wall 340 (bouncing the spaceship off the wall awards stars 310 as indicated in FIG. 7C) and into a wall gap 350 that contains stars 310 (which are then collected when encountered by the spaceship 300 as indicated in FIG. 7C). Note that a star counter 400 increases from an amount in FIG. 7A to a higher amount in FIG. 7B and an even higher amount in FIG. 7C as the stars 310 are awarded.

3.2.3.3.1. Incentive Effecting the Mechanism of Action

Preferably, with regard to the user incentive effecting a mechanism of action that treats the condition, the mechanism of action includes one or more of (1) training the user to reduce an input time period and (2) rewarding the user for reducing the input time period, wherein the input time period is a time period between the display of the response invitation indicator and the receiving of the user input.

In the example embodiment, the at least one user input aspect of the user input related to the display of the spaceship includes an input time period (referred to in the example embodiment as the Reaction Time), which is the time that passes between the display of the spaceship and the receipt of the touch input on the touch screen at the location of the spaceship. Shorter Reaction Times are correlated with a greater attentional bias towards the stimulus image that occupied the spaceship location prior to the display of the spaceship. In the example embodiment, the non-threatening Facial Stimulus occupies the spaceship location prior to the display of the spaceship.

3.2.3.3.1.1. Training to Reduce Input Time Period

Preferably, with regard to the mechanism of action including training the user to reduce an input time period, training the user to reduce the input time period includes comparing the input time period to an incentive time period and, when the input time period is related to the incentive time period in accordance with a predetermined formula, decreasing the incentive time period for a subsequent turn. Preferably, when the input time period is less than the incentive time period, the incentive time period is decreased for a subsequent turn.

Reference is again made to FIGS. 7A, 7B and 7C, which illustrate star collection during a turn of a treatment session of the example embodiment.

In the example embodiment, when the Reaction Time is related to the incentive time period (referred to in the example embodiment as the Reaction Time Threshold) in accordance with a predetermined formula, the Reaction Time Threshold is decreased for a subsequent turn. Preferably, the Reaction Time Threshold is decreased because the Reaction Time Threshold is an average of the user's historical Reaction Times.

In the example embodiment, the user is presented with a timer 410 that visual indicates the current Reaction Time Threshold and, in relation thereto, the Reaction Time achieved by the user during the turn.

3.2.3.3.1.2. Rewarding for Reducing Input Time Period

Preferably, with regard to the mechanism of action including rewarding the user for reducing the input time period, rewarding the user for reducing the input time period includes comparing the input time period to an incentive time period, and, when the input time period is related to the incentive time period in accordance with a predetermined formula, awarding the user one or more of (1) one or more rewards and (2) an opportunity to obtain one or more rewards.

Preferably, the one or more rewards includes one or more of the following valuable to the user: points, symbols, and tokens.

Preferably, a value of the one or more rewards awarded is determined at least in part by a relationship between the input time period and the incentive time period in accordance with the predetermined formula.

Preferably, a strength of the opportunity is determined at least in part by a relationship between the input time period and the incentive time period in accordance with the predetermined formula.

Reference is again made to FIGS. 7A, 7B and 7C, which illustrate star collection during a turn of a treatment session of the example embodiment.

In the example embodiment, when the Reaction Time is related to the Reaction Time Threshold in accordance with a predetermined formula, the user is provided with one or more of (1) one or more stars, and (2) an opportunity to obtain one or more stars.

In the example embodiment, with regard to providing the user with one or more stars, the predetermined formula is the following formula (referred to herein as Formula 4):

```
if RT < L then B = 5
else if RT < U then B = ROUNDUP(5 * (5/3 − RT/(0.75 * T)))
else 0
```

-continued

Where:

RT=Reaction Time

B=Speed Bonus

T=Reaction Time Threshold

L=T/2

U=T*1.25

According to Formula 4, users with shorter Reaction Times receive a "Speed Bonus" that rewards users with between 1 and 5 additional stars, depending on the duration of the Reaction Time. The Reaction Time is denoted by timer 410. Achievement of the Speed Bonus is indicated by a speed bonus indicator 420 (e.g., indicating by "+3" that a 3-star Speed Bonus has been achieved).

In the example embodiment, with regard to providing the user with an opportunity to obtain one or more stars, the predetermined formula is the following formula (referred to herein as Formula 5):

$$\text{If } RT < T \text{ then } BF = BF * 1.25$$

Where:

RT=Reaction Time

T=user's median Reaction Time

BF=ball force (or, e.g., spaceship force), where BF=12* (distance of swipe, up to 0.8 distance-units, where beyond this distance of swipe=1.0) force-units Ball mass (or, e.g., spaceship mass)=1 mass-unit Ball linear drag (or, e.g., spaceship linear drag)=0.75 drag-units According to Formula 5, the "Speed Bonus" increases the velocity of the spaceship, enabling it to travel farther and accumulate more stars before the turn ends. For example, during each turn, the user directs (by user swipe touch input) the spaceship 300 toward the periphery of the field 180, which results in the spaceship 300 doing one or more of (1) bouncing off one or more walls 340 (and collecting any stars that may be encountered in transit), and (2) passing through a wall gap 350 (and collecting any stars contained in the gap). A spaceship with increased velocity will (as compared with a spaceship with lower velocity) travel farther, and accordingly bounce off more walls more times and encounter more stars.

3.2.3.3.2. Incentive Encouraging Continued User Participation

Preferably, with regard to the user incentive encouraging continued user participation in one or more treatment sessions, the user incentive encourages user participation in one or more subsequent treatment sessions, and most preferably encourages user participation from one treatment session to another treatment session.

In the example embodiment, in the Gameplay Stage, the Difficulty Level of the game is personalized to individual user differences in participation performance, to challenge the user enough to stay engaged while not being overwhelmed by difficulty.

3.2.3.3.2.1. Difficulty Level

Preferably, a strength of the user incentive is determined at least in part by a relationship between an input time period and an incentive time period in accordance with a predetermined formula.

In the example embodiment, the predetermined formula is the following formula (referred to herein as Formula 6):

$$\text{if } RT < T \text{ then } DL = DL + 1$$
$$\text{else if } RT > T \text{ then } DL = DL - 1, DL >= 0$$

Where:

RT=Reaction Time

T=current Reaction Time Threshold

DL=current Difficulty Level

According to Formula 6, the Difficulty Level increases when the Reaction Time is less than the Reaction Time Threshold, and decreases when the Reaction Time is greater than the Reaction Time Threshold.

3.2.3.3.2.2. Star Magnet

Preferably, implementation of the user incentive includes awarding the user an opportunity to obtain at least one reward more than the user otherwise would without the opportunity. Preferably, the at least one reward more includes one or more of the following valuable to the user: points, symbols, and tokens. Preferably, a strength of the opportunity is determined at least in part by a number of the rewards obtained by the user.

Reference is again made to FIGS. 7A, 7B and 7C, which illustrate star collection during a turn of a treatment session of the example embodiment.

In the example embodiment, awarding the user an opportunity to obtain at least one reward more than the user otherwise would without the opportunity is implemented in a concept referred to sometimes as User Leveling, which can be characterized by the user progressing to increasingly higher user states, or levels, with each level having user benefits greater than the previous level, as the user progresses through treatment sessions and over a course of treatment.

In the example embodiment, the current user level is indicated by a user level indicator 390.

Figures 8A, 8B, 8C:
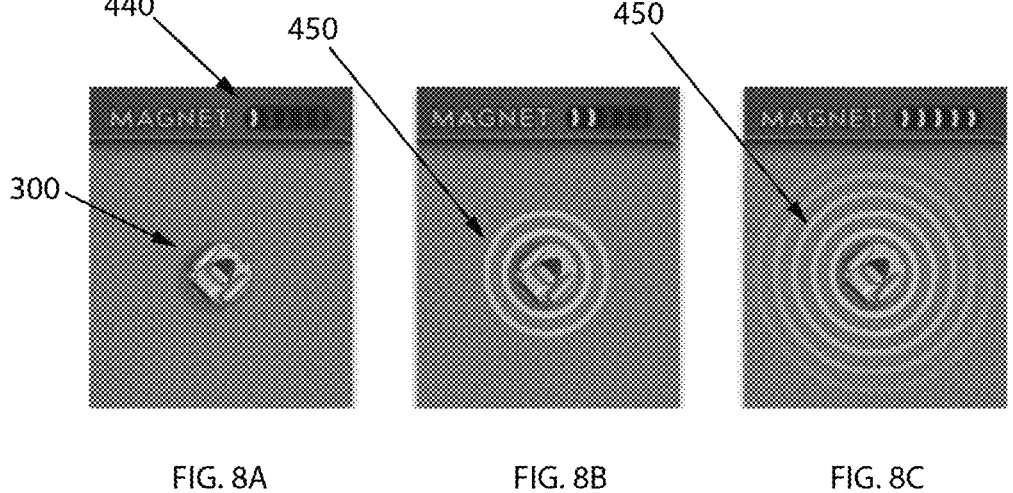
FIGS. 8A, 8B and 8C illustrate a Star Magnet feature of the example embodiment of the present invention.

Reference is now also made to FIGS. 8A, 8B and 8C, which illustrate a Star Magnet feature of the example embodiment.

In the example embodiment, the opportunity is effected by way of a feature of spaceship that is referred to as a Star Magnet. A purpose of the Star Magnet feature is to reward the user by increasing the ability of the user to collect more stars. It can function as an engagement tool to help keep a user adherent within a treatment session and throughout a course of treatment by enabling the user to progressively collect more stars than the user otherwise would without the feature.

In the example embodiment, as the user accrues stars, the user progresses to increasingly higher user states, or user levels (this progression is sometimes referred to herein as the user "leveling up"). As the user levels up, the Star Magnet increases in power (e.g., in strength, effectiveness) (this increase is sometimes referred to herein as the Star Magnet "powering up"). That is, the Star Magnet powers up to greater and greater effectiveness as the user collects stars during a session, and as the user levels up over a course of treatment.

In the example embodiment, the spaceship 300 has associated with it a Star Magnet with a magnet area (e.g., a zone, field) around it (sometimes referred to herein as a "hit box", although the area can be of any desired dimension or shape). The magnet area is indicated by lines 450, with increasing area being indicated by an increasing number of lines. When the magnet area of the spaceship overlaps with a star, the star is collected. In the example embodiment, the magnet area of the spaceship is a magnet radius, and the magnet radius varies with the user level. The user level establishes the magnet's base power and the user's intra-session collection of stars establishes the magnet's bonus power. The magnet's bonus power is indicated by the magnet bonus power indicator 440.

In the example embodiment, as the user collects stars during a session, the magnet power varies in size according to the following formula (referred to herein as Formula 9):

$$\text{Magnet Power=Base Power+Bonus Power}$$

The base power of the magnet varies as follows:
At a user level of <6, the magnet has a base power of 0.25 units
At a user level between 6 and 15, the magnet has a base power of 0.35 units
At a user level between 16 and 24, the magnet has a base power of 0.55 units
At a user level greater than 25, the magnet has a base power of 0.80 units
The bonus power of the magnet varies according to the formula:

$$\text{Bonus radius=Stars collected*0.0003}$$

The magnet power is then used to determine the magnet radius. There are 5 different segmented radius levels based on the following:
At a magnet power less than 0.35, the magnet has a radius of 0.25 units
At a magnet power between 0.35 and 0.55, the magnet has a radius of 0.35 units
At a magnet power between 0.55 and 0.80, the magnet has a radius of 0.55 units
At a magnet power between 0.80 and 1.15, the magnet has a radius of 0.80 units
At a magnet power greater than or equal to 1.15, the magnet has a radius of 1.15 units

3.2.3.3.2.3. Dynamic Environment

Further with regard to the user incentive encouraging continued user participation in one or more treatment sessions, certain preferred embodiments further include, in connection with the display of the response invitation indicator, displaying an environment having at least one environment characteristic inviting interaction by the user, and implementation of the user incentive includes changing the at least one environment characteristic, the at least one environment characteristic including one or more of dynamism, complexity, interestingness, and challenge.

Reference is again made to FIGS. 7A, 7B and 7C, which illustrate star collection during a turn of a treatment session of the example embodiment.

In the example embodiment, increasingly higher Difficulty Levels correlate to increasingly inviting environment characteristic changes. For example, higher Difficulty Levels present environments that are more dynamic, complex, interesting, and/or challenging than environments of lower Difficulty Levels.

In some of those certain and other preferred embodiments, the at least one environment characteristic is manifest at a periphery of the environment.

In the example embodiment, a border, or wall 340, is displayed along a periphery of the fixed rectangular field 180 within which the Fixation Point, Facial Stimuli, and Gameplay Stimulus (e.g., the spaceship) are displayed. The wall 340 includes one or more (preferably three) wall openings or gaps, and each gap 350 contains a randomized number of stars 310. During the Gameplay Stage, the user directs (by user swipe touch input) the spaceship 300 toward the periphery of the field 180, which results in the spaceship doing one or more of (1) bouncing off one or more walls 340 (and collecting any stars 310 that may be encountered in transit), and (2) passing through a wall gap 350 (and collecting any stars 310 contained in the gap).

In the example embodiment, at least two elements of this environment become increasingly more inviting to the user with increasing Difficulty Levels: (1) a speed of the wall 340 traveling along the periphery of the field 180 increases (and accordingly the wall gaps 350 travel at greater speeds along the periphery of the field 180), and (2) the wall gaps 340 reduce in size faster over the duration of the turn.

In the example embodiment, the relationship of the wall gap travel speed to the Difficulty Level is governed by the following formula (referred to herein as Formula 7):

$$\text{let } t=\min(\max(DL/W,0),1)$$

$$S=(1-t)*\text{Min } S+t*\text{Max } S$$

Where:
DL=Difficulty Level
W=threshold for max gap speed
Min S=minimum gap speed
Max S=maximum gap speed
In the example embodiment, the relationship of the wall gap shrinking speed to the Difficulty Level is governed by the following formula (referred to herein as Formula 8):

$$\text{let } t=\min(\max(DL/L,0),1)$$

$$S=GS/\max(((1-t)*\text{Max } C+t*\text{Min } C),(M*R))$$

Where:
DL=Difficulty Level
L=threshold for minimum gap collapse time
Max C=maximum amount of time
Min C=minimum amount of time
GS=gap size
M=Reaction time multiplier
R=Median Reaction Time
S=Gap-closing speed
In the example embodiment, the dynamics effected by Formula 7 and Formula 8 enable a dynamic gameplay environment that helps to keep users engaged in the treatment as their proficiency in the game aspects improves.

In some of those certain and other preferred embodiments, the at least one environment characteristic is manifest between the response invitation indicator and the periphery of the environment.

Reference is again made to FIGS. 7A, 7B and 7C, which illustrate star collection during a turn of a treatment session of the example embodiment.

In the example embodiment, stars 310 are not only present in the wall gaps 340, but also appear in the field 180 at locations between the spaceship 300 and the wall 340, and the spaceship 300 can collect stars it encounters during transit across the field 180. The number and size of stars can change during a turn, and from one turn to another.

In some of those certain and other preferred embodiments, the changing occurs during the turn.

For example, in the example embodiment, the wall gaps 340 shrink during the turn, as discussed above.

In some of those certain and other preferred embodiments, the changing occurs from one turn to a subsequent turn.

For example, in the example embodiment, the wall gap travel speed remains the same during a turn but is different for subsequent turns if the Difficulty Level has changed between the turns.

In some of those certain and other preferred embodiments, the changing results from the interaction by the user. Preferably, the changing is determined at least in part by a relationship between an input time period and an incentive time period in accordance with a predetermined formula.

For example, in the example embodiment, the changing results from changes in the Difficulty Level, which is governed by Formula 6 (set forth above).

3.2.3.3.2.4. Targets

Preferably, display of the environment includes displaying at least one target, each at a respective target location in the display field, wherein the target has at least one target characteristic, and wherein implementation of the user incentive includes changing the at least one target characteristic. Preferred targets include but are not limited to targets that depict one or more of a star, a wall, and a wall opening.

Preferably, the at least one target characteristic includes one or more of a size and a velocity, and wherein implementation of the user incentive includes one or more of (1) increasing the velocity of the target and (2) increasing a speed at which the size of the target shrinks during the turn. Preferably, the velocity of the target is determined at least in part by a relationship between an input time period and an incentive time period in accordance with a predetermined formula. Preferably, the speed at which the size of the target shrinks during the turn is determined at least in part by a relationship between an input time period and an incentive time period in accordance with a predetermined formula.

Reference is again made to FIGS. 7A, 7B and 7C, which illustrate star collection during a turn of a treatment session of the example embodiment.

As discussed above, in the example embodiment, various targets are displayed in the environment: stars 310, a wall 340, and wall gaps 350. The wall 340 is displayed along a periphery of the fixed rectangular field 180 within which the Fixation Point, Facial Stimuli, and Gameplay Stimulus (e.g., the spaceship) are displayed. The wall 340 includes the wall gaps 350, and each gap 350 contains a randomized number of stars 310. In addition, stars 310 also appear in the field 180 at locations between the spaceship 300 and the wall 340.

In the example embodiment, implementation of the user incentive includes changing one or more characteristics of the targets. For example, the number, size, and movement speed and/or direction of the stars 310 can be changed, during a turn and/or from one turn to another. Further, for example, the speed and/or movement direction of the wall 340 can be changed, during a turn and/or from one turn to another. Further, for example, the size, speed and/or movement direction of the wall gaps 350 can be changed, during a turn and/or from one turn to another. Further, for example, the number of stars 310 contained in the wall gaps 350 can be changed, during a turn and/or from one turn to another.

Further as discussed above, in the example embodiment, the following changes occur with increasing Difficulty Levels: (1) a speed of the wall 340 traveling along the periphery of the field 180 increases (and accordingly the wall gaps 350 travel at greater speeds along the periphery of the field 180), and (2) the wall gaps 350 reduce in size faster over the duration of the turn. As discussed above, in the example embodiment, the relationship of the wall gap travel speed to the Difficulty Level is governed by Formula 7 (set forth above). As discussed above, in the example embodiment, the relationship of the wall gap shrinking speed to the Difficulty Level is governed by Formula 8 (set forth above).

3.3. Pause Control

In preferred embodiments, a pause function allows users to pause a turn, session or other progression of the treatment. Preferably, when the pause function is activated, a timer imposes a pause time limit. Further preferably, if the pause time limit is exceeded, the user is prevented from resuming or starting treatment until a period of time has passed. This period of time can be predetermined and/or determined based on user interaction during the treatment.

Figure 9:
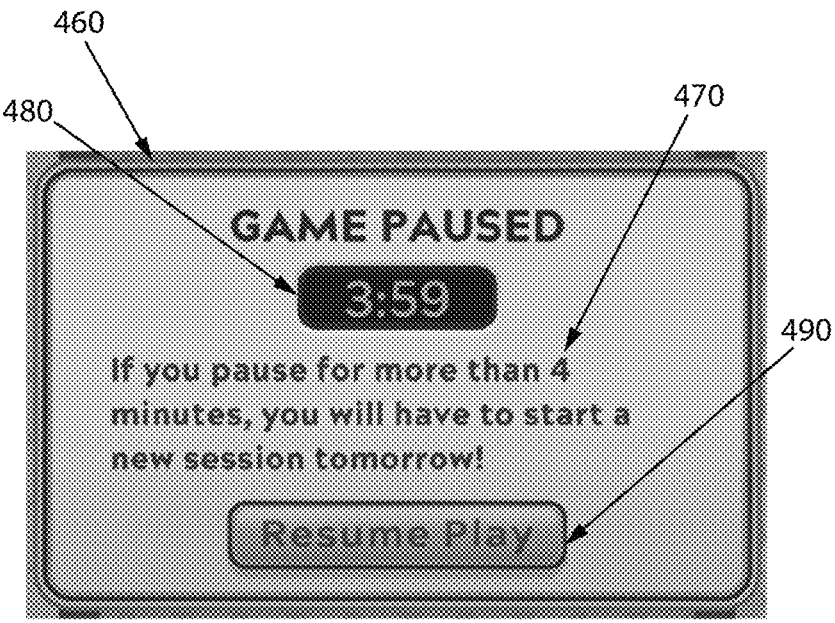
FIG. 9 illustrates a pause time limit notification of the example embodiment of the present invention.

Reference is now made to FIG. 9, which illustrates a pause time limit notification of the example embodiment. In the example embodiment, when the user pauses treatment (e.g., during a turn, session, or other activity), a pause time limit notification 460 is displayed. The pause time limit notification 460 notifies the user that a pause time limit is being imposed. As part of or otherwise in connection with the pause time limit notification 460, a pause time limit indicator 470 is displayed, along with a countdown timer 480, and a resumption selector 490. The pause time limit indicator indicates to the user the time period of the pause time limit (e.g., 4 minutes). The countdown timer 480 tracks the remaining pause time while the pause is active. The resumption selector 490 can be selected by the user to terminate the pause and resume treatment. However, if the pause time exceeds the pause time limit, the user is not permitted to resume or start treatment until the next day.

4. Computer System Components

While the example embodiment is described in connection with a mobile application running on a smartphone, it should be understood that the present invention can be implemented in any suitable apparatus. Example components that are in addition to, alternative to and/or complementary to other components described herein will now be described.

Preferred systems can include at least one user computing device in operable connection with a user network, and an application server in operable communication with the user network, the application server configured to host an application system for providing the described steps and/or functions of the present invention. The application system includes a user interface for providing access to the application system through the user computing device, wherein the application system is in communication with a display module to display the described images and features.

Preferred embodiments reside primarily in combinations of components and procedures related to the system. Accordingly, the system components have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein.

In this disclosure, the various embodiments may be a system, method, and/or computer program product at any possible technical detail level of integration. A computer program product can include, among other things, a computer-readable storage medium having computer-readable program instructions thereon for causing a processor to carry out aspects of the present disclosure.

Figure 10:
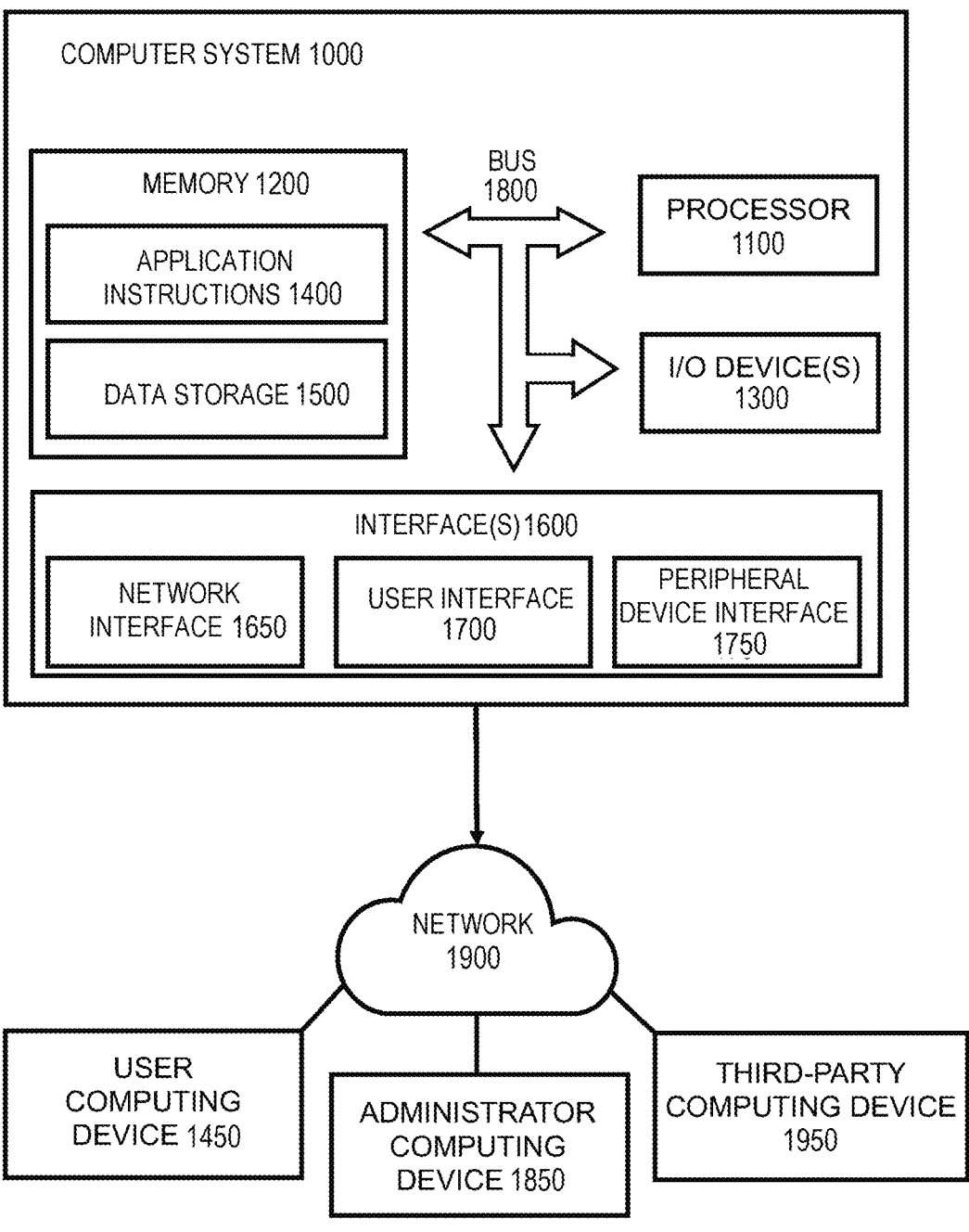
FIG. 10 illustrates a block diagram of a computing system, in accordance with certain embodiments of the present invention.

Reference is now made to FIG. 10, which illustrates a block diagram of a computing system, in accordance with certain embodiments of the present invention. The computer system 1000 may be utilized to execute various procedures, including the processes described herein. The computer system 1000 comprises a standalone computer or mobile computing device, a mainframe computer system, a workstation, a network computer, a desktop computer, a laptop, or the like. The computing device 1000 can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive).

In some embodiments, the computer system 1000 includes one or more processors 1100 coupled to a memory 1200 through a system bus 1800 that couples various system components, such as an input/output (I/O) devices 1300, to the processors 1100. The bus 1800 may be any of several types of bus structures including a memory bus or memory controller, a peripheral bus, and a local bus using any of a variety of bus architectures. For example, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

In some embodiments, the computer system 1000 includes one or more input/output (I/O) devices 1300, such as video device(s) (e.g., a camera), audio device(s), and display(s) are in operable communication with the computer system 1000. In some embodiments, similar I/O devices 1300 may be separate from the computer system 1000 and may interact with one or more nodes of the computer system 100 through a wired or wireless connection, such as over a network interface.

Processors 1100 suitable for the execution of computer readable program instructions include both general and special purpose microprocessors and any one or more processors of any digital computing device. For example, each processor 1100 may be a single processing unit or a number of processing units and may include single or multiple computing units or multiple processing cores. The processor(s) 1100 can be implemented as one or more microprocessors, microcomputers, microcontrollers, digital signal processors, central processing units, state machines, logic circuitries, and/or any devices that manipulate signals based on operational instructions. For example, the processor(s) 1100 may be one or more hardware processors and/or logic circuits of any suitable type specifically programmed or configured to execute the algorithms and processes described herein. The processor(s) 1100 can be configured to fetch and execute computer readable program instructions stored in the computer-readable media, which can program the processor(s) 1100 to perform the functions described herein.

In this disclosure, the term "processor" can refer to substantially any computing processing unit or device, including single-core processors, single-processors with software multithreading execution capability, multi-core processors, multi-core processors with software multithreading execution capability, multi-core processors with hardware multithread technology, parallel platforms, and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures, such as molecular and quantum-dot based transistors, switches, and gates, to optimize space usage or enhance performance of user equipment. A processor can also be implemented as a combination of computing processing units.

In some embodiments, the memory 1200 includes computer-readable application instructions 1500, configured to implement certain embodiments described herein, and a database 1500, comprising various data accessible by the application instructions 1400. In some embodiments, the application instructions 1400 include software elements corresponding to one or more of the various embodiments described herein. For example, application instructions 1400 may be implemented in various embodiments using any desired programming language, scripting language, or combination of programming and/or scripting languages (e.g., C, C++, C #, JAVA, JAVASCRIPT, PERL, etc.).

In this disclosure, terms "store," "storage," "data store," data storage," "database," and substantially any other information storage component relevant to operation and functionality of a component are utilized to refer to "memory components," which are entities embodied in a "memory," or components comprising a memory. Those skilled in the art would appreciate that the memory and/or memory components described herein can be volatile memory, nonvolatile memory, or both volatile and nonvolatile memory. Nonvolatile memory can include, for example, read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include, for example, RAM, which can act as external cache memory. The memory and/or memory components of the systems or computer-implemented methods can include the foregoing or other suitable types of memory.

Generally, a computing device will also include, or be operatively coupled to receive data from or transfer data to, or both, one or more mass data storage devices; however, a computing device need not have such devices. The computer readable storage medium (or media) can be a tangible device that can retain and store instructions for use by an instruction execution device. The computer readable storage medium can be, for example, an electronic storage device, a magnetic storage device, an optical storage device, an electromagnetic storage device, a semiconductor storage device, or any suitable combination of the foregoing. A non-exhaustive list of more specific examples of the computer readable storage medium can include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. In this disclosure, a computer readable storage medium is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

In some embodiments, the steps and actions of the application instructions 140 described herein are embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor 1100 such that the processor 1100 can read information from, and write information to, the storage medium. In the alternative, the storage medium may be integrated into the processor 1100. Further, in some embodiments, the processor 1100 and the storage medium may reside in an Application Specific Integrated Circuit (ASIC). In the alternative, the processor and the storage medium may reside as discrete components in a computing device. Additionally, in some embodiments, the events or actions of a method or algorithm may reside as one or any combination or set of codes and instructions on a machine-readable medium or computer-readable medium, which may be incorporated into a computer program product.

In some embodiments, the application instructions 1400 for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The application instructions 1400 can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

In some embodiments, the application instructions 1400 can be downloaded to a computing/processing device from a computer readable storage medium, or to an external computer or external storage device via a network 1900. A network adapter card or network interface in each computing/processing device receives computer readable program instructions from the network and forwards the computer readable application instructions 1400 for storage in a computer readable storage medium within the respective computing/processing device.

In some embodiments, the computer system 1000 includes one or more interfaces 160 that allow the computer system 1000 to interact with other systems, devices, or computing environments. In some embodiments, the computer system 1000 comprises a network interface 1650 to communicate with a network 1900. In some embodiments, the network interface 1650 is configured to allow data to be exchanged between the computer system 100 and other devices attached to the network 1900, such as other computer systems, or between nodes of the computer system 1000. In various embodiments, the network interface 1650 may support communication via wired or wireless general data networks, such as any suitable type of Ethernet network, for example, via telecommunications/telephony networks such as analog voice networks or digital fiber communications networks, via storage area networks such as Fiber Channel SANs, or via any other suitable type of network and/or protocol. Other interfaces include the user interface 1700 and the peripheral device interface 1750.

In some embodiments, the network 1900 corresponds to a local area network (LAN), wide area network (WAN), the Internet, a direct peer-to-peer network (e.g., device to device Wi-Fi, Bluetooth, etc.), and/or an indirect peer-to-peer network (e.g., devices communicating through a server, router, or other network device). The network 1900 can comprise copper transmission cables, optical transmission fibers, wireless transmission, routers, firewalls, switches, gateway computers and/or edge servers. The network 1900 can represent a single network or multiple networks. In some embodiments, the network 1900 used by the various devices of the computer system 100 is selected based on the proximity of the devices to one another or some other factor. For example, when a first user device and second user device are near each other (e.g., within a threshold distance, within direct communication range, etc.), the first user device may exchange data using a direct peer-to-peer network. But when the first user device and the second user device are not near each other, the first user device and the second user device may exchange data using a peer-to-peer network (e.g., the Internet). The Internet refers to the specific collection of networks and routers communicating using an Internet Protocol ("IP") including higher level protocols, such as Transmission Control Protocol/Internet Protocol ("TCP/IP") or the Uniform Datagram Packet/Internet Protocol ("UDP/IP").

Any connection between the components of the system may be associated with a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. As used herein, the terms "disk" and "disc" include compact disc (CD), laser disc, optical disc, digital versatile disc (DVD), floppy disk, and Blu-ray disc; in which "disks" usually reproduce data magnetically, and "discs" usually reproduce data optically with lasers. Combinations of the above should also be included within the scope of computer-readable media. In some embodiments, the computer-readable media includes volatile and nonvolatile memory and/or removable and non-removable media implemented in any type of technology for storage of information, such as computer-readable instructions, data structures, program modules, or other data. Such computer-readable media may include RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the computing device, the computer-readable media may be a type of computer-readable storage media and/or a tangible non-transitory media to the extent that when mentioned, non-transitory computer-readable media exclude media such as energy, carrier signals, electromagnetic waves, and signals per se.

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

In some embodiments, the system can also be implemented in cloud computing environments. In this context, "cloud computing" refers to a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

As used herein, the term "add-on" (or "plug-in") refers to computing instructions configured to extend the functionality of a computer program, where the add-on is developed specifically for the computer program. The term "add-on data" refers to data included with, generated by, or organized by an add-on. Computer programs can include computing instructions, or an application programming interface (API) configured for communication between the computer program and an add-on. For example, a computer program can be configured to look in a specific directory for add-ons developed for the specific computer program. To add an add-on to a computer program, for example, a user can download the add-on from a website and install the add-on in an appropriate directory on the user's computer.

In some embodiments, the computer system 1000 may include a user computing device 145, an administrator computing device 1850 and a third-party computing device 1950 each in communication via the network 1900. The user computing device 1450 may be utilized by a patient interacting with an embodiment of the present invention. The administrator computing device 1850 is utilized by an administrative user to moderate content and to perform other administrative functions. The third-party computing device 1950 may include any third-party in communication with the system.

Figure 11:
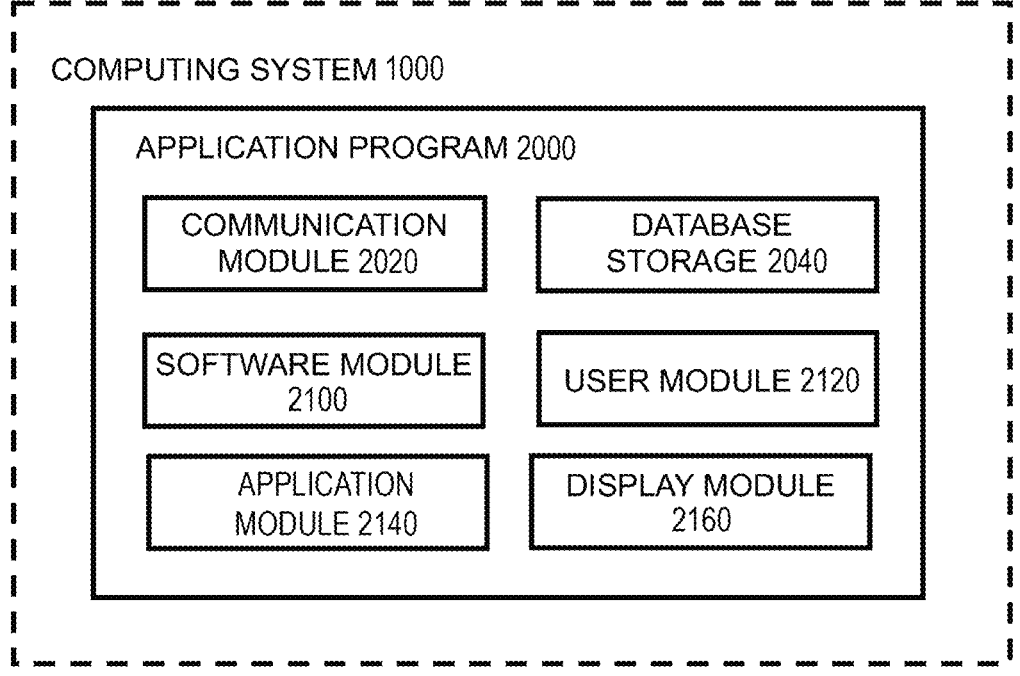
FIG. 11 illustrates a block diagram of an application program operated by the computing system of FIG. 10, in accordance with certain embodiments of the present invention.

Reference is now made to FIG. 11, which illustrates a block diagram of an application program operated by the computing system of FIG. 10, in accordance with certain embodiments of the present invention. The computing system 1000 operating the application program 2000 comprises one or more modules having the necessary routines and data structures for performing specific tasks, and one or more engines configured to determine how the platform manages and manipulates data. In some embodiments, the application program 2000 comprises one or more of a communication module 2020, a database engine 2040, a verification module 2100, a user module 2120, a treatment application module 2140, a display module 2160, a video module 2180, and a purchase tracking module 2200.

In some embodiments, the communication module 2020 is configured for receiving, processing, and transmitting a user command and/or one or more data streams. In such embodiments, the communication module 2020 performs communication functions between various devices, including the user computing device 1450, the administrator computing device 1850, and a third-party computing device 1950. In some embodiments, the communication module 2020 is configured to allow one or more users of the system, including a third-party, to communicate with one another. In some embodiments, the communications module 2020 is configured to maintain one or more communication sessions with one or more servers, the administrative computing device 1850, and/or one or more third-party computing device(s) 1950.

In some embodiments, a database engine 2040 is configured to facilitate the storage, management, and retrieval of data to and from one or more storage mediums, such as the one or more internal databases described herein. In some embodiments, the database engine 2040 is coupled to an external storage system. In some embodiments, the database engine 2040 is configured to apply changes to one or more databases. In some embodiments, the database engine 2040 comprises a search engine component for searching through thousands of data sources stored in different locations.

In some embodiments, the software module 2100 allows for is in communication with the application program 200 to provide a means for implementing the treatment described hereinabove.

In some embodiments, the user module 2120 facilitates the creation of a user account for the application system. The user module 2120 may allow the user to create a user profile which includes user information, user preferences, establish user credentials, and the like.

In some embodiments, the treatment application module 2140 is in operable communication with the computing system to provide the treatment experience described hereinabove. The treatment application module 2140 may be in operable communication with the communication module 2020 to transmit results from the user's interactions with the system.

In some embodiments, the display module 2160 is configured to display one or more graphic user interfaces, including, e.g., one or more user interfaces, one or more consumer interfaces, one or more video presenter interfaces, etc. In some embodiments, the display module 2160 is configured to temporarily generate and display various pieces of information in response to one or more commands or operations. The various pieces of information or data generated and displayed may be transiently generated and displayed, and the displayed content in the display module 2160 may be refreshed and replaced with different content upon the receipt of different commands or operations in some embodiments. In such embodiments, the various pieces of information generated and displayed in a display module 2160 may not be persistently stored.

Exemplary screenshots of the user interface with which the user interacts are illustrated in figures described above. During use, the system displays the treatment environment which displays various images and elements as described above in connection with the figures.

In this disclosure, the various embodiments are described with reference to the flowchart illustrations and/or block diagrams of methods, apparatus (systems), and computer program products. Those skilled in the art would understand that each block of the flowchart illustrations and/or block diagrams, and combinations of blocks in the flowchart illustrations and/or block diagrams, can be implemented by computer readable program instructions. The computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram block or blocks. The computer readable program instructions can be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can be loaded onto a computer, other programmable data processing apparatus, or other device to cause a series of operational acts to be performed on the computer, other programmable apparatus, or other device to produce a computer implemented process, such that the instructions that execute on the computer, other programmable apparatus, or other device implement the functions or acts specified in the flowchart and/or block diagram block or blocks.

In this disclosure, the block diagrams in the Figures illustrate the architecture, functionality, and operation of possible implementations of systems, methods, and computer program products according to the various embodiments. Each block in the flowchart or block diagrams can represent a module, segment, or portion of instructions, which comprises one or more executable instructions for implementing the specified logical function(s). In some embodiments, the functions noted in the blocks can occur out of the order noted in the figures. For example, two blocks shown in succession can, in fact, be executed concurrently or substantially concurrently, or the blocks can sometimes be executed in the reverse order, depending upon the functionality involved. In some embodiments, each block of the block diagrams and/or flowchart illustration, and combinations of blocks in the block diagrams and/or flowchart illustration, can be implemented by a special purpose hardware-based system that performs the specified functions or acts or carry out combinations of special purpose hardware and computer instructions.

In this disclosure, the subject matter has been described in the general context of computer-executable instructions of a computer program product running on a computer or computers, and those skilled in the art would recognize that this disclosure can be implemented in combination with other program modules. Generally, program modules include routines, programs, components, data structures, etc. that perform particular tasks and/or implement particular abstract data types. Those skilled in the art would appreciate that the computer-implemented methods disclosed herein can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated embodiments can be practiced in distributed computing environments where tasks are performed by remote processing devices that are linked through a communications network. Some embodiments of this disclosure can be practiced on a stand-alone computer. In a distributed computing environment, program modules can be located in both local and remote memory storage devices.

In this disclosure, the terms "component," "system," "platform," "interface," and the like, can refer to and/or include a computer-related entity or an entity related to an operational machine with one or more specific functionalities. The disclosed entities can be hardware, a combination of hardware and software, software, or software in execution. For example, a component can be a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As another example, a component can be an apparatus that provides specific functionality through electronic components without mechanical parts, wherein the electronic components can include a processor or other means to execute software or firmware that confers at least in part the functionality of the electronic components. In some embodiments, a component can emulate an electronic component via a virtual machine, e.g., within a cloud computing system.

The phrase "application" as is used herein means software other than the operating system, such as Word processors, database managers, Internet browsers and the like. Each application generally has its own user interface, which allows a user to interact with a particular program. The user interface for most operating systems and applications is a graphical user interface (GUI), which uses graphical screen elements, such as windows (which are used to separate the screen into distinct work areas), icons (which are small images that represent computer resources, such as files), pull-down menus (which give a user a list of options), scroll bars (which allow a user to move up and down a window) and buttons (which can be "pushed" with a click of a mouse). A wide variety of applications is known to those in the art.

The phrases "Application Program Interface" and API as are used herein mean a set of commands, functions and/or protocols that computer programmers can use when building software for a specific operating system. The API allows programmers to use predefined functions to interact with an operating system, instead of writing them from scratch. Common computer operating systems, including Windows, Unix, and the Mac OS, usually provide an API for programmers. An API is also used by hardware devices that run software programs. The API generally makes a programmer's job easier, and it also benefits the end user since it generally ensures that all programs using the same API will have a similar user interface.

The phrase "central processing unit" as is used herein means a computer hardware component that executes individual commands of a computer software program. It reads program instructions from a main or secondary memory, and then executes the instructions one at a time until the program ends. During execution, the program may display information to an output device such as a monitor.

The term "execute" as is used herein in connection with a computer, console, server system or the like means to run, use, operate or carry out an instruction, code, software, program and/or the like.

5. Broad Scope

Accordingly, while the present invention may be described in terms of specific embodiments, the present invention is not limited to these disclosed embodiments. Upon reading this disclosure, many modifications and other embodiments of the present invention will come to mind of those skilled in the art to which this invention pertains, and those are intended to be and are covered by this disclosure and the appended claims. The scope of the present invention should be determined by proper interpretation and construction of the appended claims and their legal equivalents, as understood by those of skill in the art relying upon the disclosure in this specification and the attached drawings.

6. Claim Language Supporting Paragraphs

The following paragraphs describe certain preferred embodiments of the present invention in claim language format.

1. A computing system, comprising:
   one or more processors;
   memory; and
   one or more programs, wherein the one or more programs are stored in the memory and are configured to be executed by the one or more processors to treat a subject in need of treatment of a psychiatric condition, the one or more programs including instructions for providing a therapy session, the therapy session comprising a plurality of sequential turns, each turn comprising:
   (i) displaying, for a predetermined focal point indicator display time period and thereafter terminating the displaying of, a focal point indicator at a focal point indicator location in a display area of a display;
   (ii) after terminating the display of the focal point indicator, displaying, together for a predetermined stimulus display time period and thereafter terminating the display of, first and second stimulus images at respective first and second stimulus image locations in the display area of the display, the first and second stimulus images being associated with respective first and second stimuli, the first and second stimulus image locations being of equal prominence in relation to the focal point indicator location;
   (iii) after terminating the display of the first and second stimulus images, displaying in connection with the first stimulus image location a response invitation indicator;
   (iv) receiving a user input in response to the display of the response invitation indicator;
   (v) determining at least one user input aspect of the user input related to the display of the response invitation indicator; and
   (vi) when the at least one user input aspect has at least one desired characteristic, implementing a user incentive to modify the user input aspect for a subsequent turn.

2. The computing system of claim 1, wherein the therapy session is defined by a predetermined number of turns.
3. The computing system of claim 2, wherein the predetermined number of turns is 180.
4. The computing system of claim 1, wherein the therapy session is defined by a number of turns that is determined during the therapy session based on the at least one user input aspect of the user input.
5. The computing system of claim 1, wherein the focal point indicator location is randomized at each turn.
6. The computing system of claim 1, wherein the predetermined focal point indicator display time period is 500 ms.
7. The computing system of claim 1, wherein the predetermined stimulus display time period is inclusively between 500 ms and 1 second.
8. The computing system of claim 7, wherein the predetermined stimulus display time period is 500 ms.
9. The computing system of claim 1, wherein the first and second stimulus images are configured to induce human amygdala activation.
10. The computing system of claim 1, wherein the first and second stimulus images are associated with respective first and second emotional states.
11. The computing system of claim 10, wherein the first stimulus image is associated with a non-threatening emotional state and the second stimulus image is associated with a threatening emotional state.
12. The computing system of claim 10, wherein the first stimulus image depicts a non-threatening facial expression and the second stimulus image depicts a threatening facial expression.
13. The computing system of claim 10, wherein the first stimulus image depicts a pleasant facial expression and the second stimulus image depicts an unpleasant facial expression.
14. The computing system of claim 10, wherein the first stimulus image depicts a happy facial expression and the second stimulus image depicts a sad facial expression.
15. The computing system of claim 1, wherein the first and second stimulus image locations are equidistant from the focal point indicator location.
16. The computing system of claim 15, wherein a distance between the first and second stimulus image locations is randomized at each turn.
17. The computing system of claim 15, wherein the first and second stimulus image locations are aligned with one another and the focal point indicator location.
18. The computing system of claim 17, wherein an angle of the alignment is randomized at each turn.
19. The computing system of claim 1, wherein the response invitation indicator is displayed at the first stimulus location.
20. The computing system of claim 1, wherein the response invitation indicator depicts a ball or a spaceship.
21. The computing system of claim 1, wherein the response invitation indicator is displayed at a response invitation indicator location in the display area of the display and the user input includes touch input at the response invitation indicator location.
22. The computing system of claim 21, wherein the touch input includes a swiping touch input.
23. The computing system of claim 22, wherein the swiping touch input has at least one of a direction aspect and a velocity aspect.

24. The computing system of claim 1, wherein the user incentive effects a mechanism of action that treats the condition.

25. The computing system of claim 24, wherein the mechanism of action includes one or more of (1) training the user to reduce an input time period and (2) rewarding the user for reducing the input time period, wherein the input time period is a time period between the display of the response invitation indicator and the receiving of the user input.

26. The computing system of claim 25, wherein training the user to reduce the input time period includes comparing the input time period to an incentive time period and, when the input time period is related to the incentive time period in accordance with a predetermined formula, decreasing the incentive time period for a subsequent turn.

27. The computing system of claim 26, wherein when the input time period is less than the incentive time period, the incentive time period is decreased for a subsequent turn.

28. The computing system of claim 25, wherein rewarding the user for reducing the input time period includes comparing the input time period to an incentive time period, and, when the input time period is related to the incentive time period in accordance with a predetermined formula, awarding the user one or more of (1) one or more rewards and (2) an opportunity to obtain one or more rewards.

29. The computing system of claim 28, wherein the one or more rewards includes one or more of the following valuable to the user: points, symbols, and tokens.

30. The computing system of claim 28, wherein a value of the one or more rewards awarded is determined at least in part by a relationship between the input time period and the incentive time period in accordance with the predetermined formula.

31. The computing system of claim 28, wherein a strength of the opportunity is determined at least in part by a relationship between the input time period and the incentive time period in accordance with the predetermined formula.

32. The computing system of claim 1, wherein the user incentive encourages continued user participation in one or more treatment sessions.

33. The computing system of claim 32, wherein the user incentive encourages user participation in one or more subsequent treatment sessions.

34. The computing system of claim 33, wherein the user incentive encourages user participation from one treatment session to another treatment session.

35. The computing system of claim 32, wherein a strength of the user incentive is determined at least in part by a relationship between an input time period and an incentive time period in accordance with a predetermined formula.

36. The computing system of claim 32, wherein implementation of the user incentive includes awarding the user an opportunity to obtain at least one reward more than the user otherwise would without the opportunity.

37. The computing system of claim 36, wherein the at least one reward more includes one or more of the following valuable to the user: points, symbols, and tokens.

38. The computing system of claim 36, wherein a strength of the opportunity is determined at least in part by a number of the rewards obtained by the user.

39. The computing system of claim 32, further comprising, in connection with the display of the response invitation indicator, displaying an environment having at least one environment characteristic inviting interaction by the user, and wherein implementation of the user incentive includes changing the at least one environment characteristic, the at least one environment characteristic including one or more of dynamism, complexity, interestingness, and challenge.

40. The computing system of claim 39, wherein the at least one environment characteristic is manifest at a periphery of the environment.

41. The computing system of claim 39, wherein the at least one environment characteristic is manifest between the response invitation indicator and the periphery of the environment.

42. The computing system of claim 39, wherein the changing occurs during the turn.

43. The computing system of claim 39, wherein the changing occurs from one turn to a subsequent turn.

44. The computing system of claim 39, wherein the changing results from the interaction by the user.

45. The computing system of claim 44, wherein the changing is determined at least in part by a relationship between an input time period and an incentive time period in accordance with a predetermined formula.

46. The computing system of claim 39, wherein display of the environment includes displaying at least one target, each at a respective target location in the display field, wherein the target has at least one target characteristic, and wherein implementation of the user incentive includes changing the at least one target characteristic.

47. The computing system of claim 46, wherein the target includes a depiction of one or more of a star, a wall, and a wall opening.

48. The computing system of claim 46, wherein the at least one target characteristic includes one or more of a size and a velocity, and wherein implementation of the user incentive includes one or more of (1) increasing the velocity of the target and (2) increasing a speed at which the size of the target shrinks during the turn.

49. The computing system of claim 48, wherein the velocity of the target is determined at least in part by a relationship between an input time period and an incentive time period in accordance with a predetermined formula.

50. The computing system of claim 48, wherein the speed at which the size of the target shrinks during the turn is determined at least in part by a relationship between an input time period and an incentive time period in accordance with a predetermined formula.

51. A non-transitory, computer readable storage medium that contains a program, which when executed by a computer, causes the computer to provide a therapy session comprising a plurality of sequential turns by carrying out actions for each turn, each turn comprising:

(i) displaying, for a predetermined focal point indicator display time period and thereafter terminating the displaying of, a focal point indicator at a focal point indicator location in a display area of a display;

(ii) after terminating the display of the focal point indicator, displaying, together for a predetermined stimulus display time period and thereafter terminating the display of, first and second stimulus images at respective first and second stimulus image locations in the display area of the display, the first and second stimulus images being associated with respective first and second stimuli, the first and second stimulus image locations being of equal prominence in relation to the focal point indicator location;

(iii) after terminating the display of the first and second stimulus images, displaying in connection with the first stimulus image location a response invitation indicator;

(iv) receiving a user input in response to the display of the response invitation indicator;

(v) determining at least one user input aspect of the user input related to the display of the response invitation indicator; and (vi) when the at least one user input aspect has at least one desired characteristic, implementing a user incentive to modify the user input aspect for a subsequent turn.

52. The medium of claim 51, wherein the therapy session is defined by a predetermined number of turns.

53. The medium of claim 52, wherein the predetermined number of turns is 180.

54. The medium of claim 51, wherein the therapy session is defined by a number of turns that is determined during the therapy session based on the at least one user input aspect of the user input.

55. The medium of claim 51, wherein the focal point indicator location is randomized at each turn.

56. The medium of claim 51, wherein the predetermined focal point indicator display time period is 500 ms.

57. The medium of claim 51, wherein the predetermined stimulus display time period is inclusively between 500 ms and 1 second.

58. The medium of claim 57, wherein the predetermined stimulus display time period is 500 ms.

59. The medium of claim 51, wherein the first and second stimulus images are configured to induce human amygdala activation.

50. The medium of claim 51, wherein the first and second stimulus images are associated with respective first and second emotional states.

61. The medium of claim 60, wherein the first stimulus image is associated with a non-threatening emotional state and the second stimulus image is associated with a threatening emotional state.

62. The medium of claim 60, wherein the first stimulus image depicts a non-threatening facial expression and the second stimulus image depicts a threatening facial expression.

63. The medium of claim 60, wherein the first stimulus image depicts a pleasant facial expression and the second stimulus image depicts an unpleasant facial expression.

64. The medium of claim 60, wherein the first stimulus image depicts a happy facial expression and the second stimulus image depicts a sad facial expression.

65. The medium of claim 51, wherein the first and second stimulus image locations are equidistant from the focal point indicator location.

66. The medium of claim 65, wherein a distance between the first and second stimulus image locations is randomized at each turn.

67. The medium of claim 65, wherein the first and second stimulus image locations are aligned with one another and the focal point indicator location.

68. The medium of claim 67, wherein an angle of the alignment is randomized at each turn.

69. The medium of claim 51, wherein the response invitation indicator is displayed at the first stimulus location.

70. The medium of claim 51, wherein the response invitation indicator depicts a ball or a spaceship.

71. The medium of claim 51, wherein the response invitation indicator is displayed at a response invitation indicator location in the display area of the display and the user input includes touch input at the response invitation indicator location.

72. The medium of claim 71, wherein the touch input includes a swiping touch input.

73. The medium of claim 72, wherein the swiping touch input has at least one of a direction aspect and a velocity aspect.

74. The medium of claim 51, wherein the user incentive effects a mechanism of action that treats the condition.

75. The medium of claim 74, wherein the mechanism of action includes one or more of (1) training the user to reduce an input time period and (2) rewarding the user for reducing the input time period, wherein the input time period is a time period between the display of the response invitation indicator and the receiving of the user input.

76. The medium of claim 75, wherein training the user to reduce the input time period includes comparing the input time period to an incentive time period and, when the input time period is related to the incentive time period in accordance with a predetermined formula, decreasing the incentive time period for a subsequent turn.

77. The medium of claim 76, wherein when the input time period is less than the incentive time period, the incentive time period is decreased for a subsequent turn.

78. The medium of claim 75, wherein rewarding the user for reducing the input time period includes comparing the input time period to an incentive time period, and, when the input time period is related to the incentive time period in accordance with a predetermined formula, awarding the user one or more of (1) one or more rewards and (2) an opportunity to obtain one or more rewards.

79. The medium of claim 78, wherein the one or more rewards includes one or more of the following valuable to the user: points, symbols, and tokens.

80. The medium of claim 78, wherein a value of the one or more rewards awarded is determined at least in part by a relationship between the input time period and the incentive time period in accordance with the predetermined formula.

81. The medium of claim 78, wherein a strength of the opportunity is determined at least in part by a relationship between the input time period and the incentive time period in accordance with the predetermined formula.

82. The medium of claim 51, wherein the user incentive encourages continued user participation in one or more treatment sessions.

83. The medium of claim 82, wherein the user incentive encourages user participation in one or more subsequent treatment sessions.

84. The medium of claim 83, wherein the user incentive encourages user participation from one treatment session to another treatment session.

85. The medium of claim 82, wherein a strength of the user incentive is determined at least in part by a relationship between an input time period and an incentive time period in accordance with a predetermined formula.

86. The medium of claim 82, wherein implementation of the user incentive includes awarding the user an opportunity to obtain at least one reward more than the user otherwise would without the opportunity.

87. The medium of claim 86, wherein the at least one reward more includes one or more of the following valuable to the user: points, symbols, and tokens.

88. The medium of claim 86, wherein a strength of the opportunity is determined at least in part by a number of the rewards obtained by the user.

89. The medium of claim 82, further comprising, in connection with the display of the response invitation indicator, displaying an environment having at least one environment characteristic inviting interaction by the user, and wherein implementation of the user incentive includes changing the at least one environment characteristic, the at least one environment characteristic including one or more of dynamism, complexity, interestingness, and challenge.

90. The medium of claim 89, wherein the at least one environment characteristic is manifest at a periphery of the environment.

91. The medium of claim 89, wherein the at least one environment characteristic is manifest between the response invitation indicator and the periphery of the environment.

92. The medium of claim 89, wherein the changing occurs during the turn.

93. The medium of claim 89, wherein the changing occurs from one turn to a subsequent turn.

94. The medium of claim 89, wherein the changing results from the interaction by the user.

95. The medium of claim 94, wherein the changing is determined at least in part by a relationship between an input time period and an incentive time period in accordance with a predetermined formula.

96. The medium of claim 89, wherein display of the environment includes displaying at least one target, each at a respective target location in the display field, wherein the target has at least one target characteristic, and wherein implementation of the user incentive includes changing the at least one target characteristic.

97. The medium of claim 96, wherein the target includes a depiction of one or more of a star, a wall, and a wall opening.

98. The medium of claim 96, wherein the at least one target characteristic includes one or more of a size and a velocity, and wherein implementation of the user incentive includes one or more of (1) increasing the velocity of the target and (2) increasing a speed at which the size of the target shrinks during the turn.

99. The medium of claim 98, wherein the velocity of the target is determined at least in part by a relationship between an input time period and an incentive time period in accordance with a predetermined formula.

100. The medium of claim 98, wherein the speed at which the size of the target shrinks during the turn is determined at least in part by a relationship between an input time period and an incentive time period in accordance with a predetermined formula.

101. A method of providing a therapy session, the therapy session comprising a plurality of sequential turns, each turn comprising:

(i) displaying, for a predetermined focal point indicator display time period and thereafter terminating the displaying of, a focal point indicator at a focal point indicator location in a display area of a display;

(ii) after terminating the display of the focal point indicator, displaying, together for a predetermined stimulus display time period and thereafter terminating the display of, first and second stimulus images at respective first and second stimulus image locations in the display area of the display, the first and second stimulus images being associated with respective first and second stimuli, the first and second stimulus image locations being of equal prominence in relation to the focal point indicator location;

(iii) after terminating the display of the first and second stimulus images, displaying in connection with the first stimulus image location a response invitation indicator;

(iv) receiving a user input in response to the display of the response invitation indicator;

(v) determining at least one user input aspect of the user input related to the display of the response invitation indicator; and (vi) when the at least one user input aspect has at least one desired characteristic, implementing a user incentive to modify the user input aspect for a subsequent turn.

102. The method of claim 101, wherein the therapy session is defined by a predetermined number of turns.

103. The method of claim 102, wherein the predetermined number of turns is 180.

104. The method of claim 101, wherein the therapy session is defined by a number of turns that is determined during the therapy session based on the at least one user input aspect of the user input.

105. The method of claim 101, wherein the focal point indicator location is randomized at each turn.

106. The method of claim 101, wherein the predetermined focal point indicator display time period is 500 ms.

107. The method of claim 101, wherein the predetermined stimulus display time period is inclusively between 500 ms and 1 second.

108. The method of claim 107, wherein the predetermined stimulus display time period is 500 ms.

109. The method of claim 101, wherein the first and second stimulus images are configured to induce human amygdala activation.

110. The method of claim 101, wherein the first and second stimulus images are associated with respective first and second emotional states.

111. The method of claim 110, wherein the first stimulus image is associated with a non-threatening emotional state and the second stimulus image is associated with a threatening emotional state.

112. The method of claim 110, wherein the first stimulus image depicts a non-threatening facial expression and the second stimulus image depicts a threatening facial expression.

113. The method of claim 110, wherein the first stimulus image depicts a pleasant facial expression and the second stimulus image depicts an unpleasant facial expression.

114. The method of claim 110, wherein the first stimulus image depicts a happy facial expression and the second stimulus image depicts a sad facial expression.

115. The method of claim 101, wherein the first and second stimulus image locations are equidistant from the focal point indicator location.

116. The method of claim 115, wherein a distance between the first and second stimulus image locations is randomized at each turn.

117. The method of claim 115, wherein the first and second stimulus image locations are aligned with one another and the focal point indicator location.

118. The method of claim 117, wherein an angle of the alignment is randomized at each turn.

119. The method of claim 101, wherein the response invitation indicator is displayed at the first stimulus location.

120. The method of claim 101, wherein the response invitation indicator depicts a ball or a spaceship.

121. The method of claim 101, wherein the response invitation indicator is displayed at a response invitation indicator location in the display area of the display and the user input includes touch input at the response invitation indicator location.

122. The method of claim 121, wherein the touch input includes a swiping touch input.

123. The method of claim 122, wherein the swiping touch input has at least one of a direction aspect and a velocity aspect.

124. The method of claim 101, wherein the user incentive effects a mechanism of action that treats the condition.

125. The method of claim 124, wherein the mechanism of action includes one or more of (1) training the user to reduce an input time period and (2) rewarding the user for reducing the input time period, wherein the input time period is a time period between the display of the response invitation indicator and the receiving of the user input.

126. The method of claim 125, wherein training the user to reduce the input time period includes comparing the input time period to an incentive time period and, when the input time period is related to the incentive time period in accordance with a predetermined formula, decreasing the incentive time period for a subsequent turn.

127. The method of claim 126, wherein when the input time period is less than the incentive time period, the incentive time period is decreased for a subsequent turn.

128. The method of claim 125, wherein rewarding the user for reducing the input time period includes comparing the input time period to an incentive time period, and, when the input time period is related to the incentive time period in accordance with a predetermined formula, awarding the user one or more of (1) one or more rewards and (2) an opportunity to obtain one or more rewards.

129. The method of claim 128, wherein the one or more rewards includes one or more of the following valuable to the user: points, symbols, and tokens.

130. The method of claim 128, wherein a value of the one or more rewards awarded is determined at least in part by a relationship between the input time period and the incentive time period in accordance with the predetermined formula.

131. The method of claim 128, wherein a strength of the opportunity is determined at least in part by a relationship between the input time period and the incentive time period in accordance with the predetermined formula.

132. The method of claim 101, wherein the user incentive encourages continued user participation in one or more treatment sessions.

133. The method of claim 132, wherein the user incentive encourages user participation in one or more subsequent treatment sessions.

134. The method of claim 133, wherein the user incentive encourages user participation from one treatment session to another treatment session.

135. The method of claim 132, wherein a strength of the user incentive is determined at least in part by a relationship between an input time period and an incentive time period in accordance with a predetermined formula.

136. The method of claim 132, wherein implementation of the user incentive includes awarding the user an opportunity to obtain at least one reward more than the user otherwise would without the opportunity.

137. The method of claim 136, wherein the at least one reward more includes one or more of the following valuable to the user: points, symbols, and tokens.

138. The method of claim 136, wherein a strength of the opportunity is determined at least in part by a number of the rewards obtained by the user.

139. The method of claim 132, further comprising, in connection with the display of the response invitation indicator, displaying an environment having at least one environment characteristic inviting interaction by the user, and wherein implementation of the user incentive includes changing the at least one environment characteristic, the at least one environment characteristic including one or more of dynamism, complexity, interestingness, and challenge.

140. The method of claim 139, wherein the at least one environment characteristic is manifest at a periphery of the environment.

141. The method of claim 139, wherein the at least one environment characteristic is manifest between the response invitation indicator and the periphery of the environment.

142. The method of claim 139, wherein the changing occurs during the turn.

143. The method of claim 139, wherein the changing occurs from one turn to a subsequent turn.

144. The method of claim 139, wherein the changing results from the interaction by the user.

145. The method of claim 144, wherein the changing is determined at least in part by a relationship between an input time period and an incentive time period in accordance with a predetermined formula.

146. The method of claim 139, wherein display of the environment includes displaying at least one target, each at a respective target location in the display field, wherein the target has at least one target characteristic, and wherein implementation of the user incentive includes changing the at least one target characteristic.

147. The method of claim 146, wherein the target includes a depiction of one or more of a star, a wall, and a wall opening.

148. The method of claim 146, wherein the at least one target characteristic includes one or more of a size and a velocity, and wherein implementation of the user incentive includes one or more of (1) increasing the velocity of the target and (2) increasing a speed at which the size of the target shrinks during the turn.

149. The method of claim 148, wherein the velocity of the target is determined at least in part by a relationship between an input time period and an incentive time period in accordance with a predetermined formula.

150. The method of claim 148, wherein the speed at which the size of the target shrinks during the turn is determined at least in part by a relationship between an input time period and an incentive time period in accordance with a predetermined formula.

FIGURE ELEMENTS treatment session 100; arrow 110; arrow 120; arrow 130; first stage/Fixation Stage 140; second stage/Facial Stimuli Stage 150; third stage/Gameplay Stage 160; focal point indicator/Fixation Point 170; field 180; arrow 190; first Facial Stimulus 200; second Facial Stimulus 210; calculated line between stimulus images 220; midpoint of calculated line 230; ends of calculated line 240,250; arrow 290; response invitation indicator/Gameplay Stimulus/spaceship 300; stars 310; FIG. 7A arrow 320; FIG. 7B arrow 330; wall 340; wall gap 350; arrow 380; arrow 390; star counter 400; reaction time timer 410; speed bonus indicator 420; user level indicator 430; magnet bonus power indicator 440; magnet radius area lines 450; pause time limit notification 460; pause time limit indicator 470; countdown timer 480; resumption selector 490

What is claimed is:

1. A computing system, comprising:

one or more processors;

memory; and one or more programs, wherein the one or more programs are stored in the memory and are configured to be executed by the one or more processors to treat a subject in need of treatment of a psychiatric condition, the one or more programs including instructions for providing a therapy session effecting treatment of the psychiatric condition, the therapy session comprising a plurality of sequential turns, each turn comprising:

(i) displaying, for a predetermined focal point indicator display time period and thereafter terminating the displaying of, a focal point indicator at a focal point indicator location in a display area of a display;

(ii) after terminating the display of the focal point indicator, displaying, together for a predetermined stimulus display time period and thereafter terminating the display of, first and second stimulus images at respective first and second stimulus image locations in the display area of the display, the first and second stimulus images being associated with respective first and second stimuli, the first and second stimulus image locations being of equal prominence in relation to the focal point indicator location;

(iii) after terminating the display of the first and second stimulus images, displaying in connection with the first stimulus image location a response invitation indicator;

(iv) receiving a user input in response to the display of the response invitation indicator;

(v) determining at least one user input aspect of the user input related to the display of the response invitation indicator; and (vi) when the at least one user input aspect has at least one desired characteristic, implementing a user incentive to modify the user input aspect for a subsequent turn;

wherein the therapy session is initially defined by a predetermined number of turns, the predetermined number of turns being determined prior to a start of the therapy session, and subsequently during the therapy session the therapy session is redefined to be defined by a lesser or greater number of turns than the predetermined number of turns;

wherein the computing system further comprises, in connection with the display of the response invitation indicator, displaying an environment having at least one environment characteristic manifest at a periphery of the environment and inviting interaction by the user, the at least one environment characteristic including one or more of dynamism, complexity, interestingness, and challenge; and wherein the user incentive encourages continued user participation in one or more treatment sessions;

implementation of the user incentive includes changing the at least one environment characteristic as a result of the interaction by the user, such that the changing is determined at least in part by a relationship between an input time period and an incentive time period in accordance with a predetermined formula;

display of the environment to manifest the at least one environment characteristic includes displaying at least one target, each having at least one target characteristic including one or more of a size and a velocity;

the at least one target includes a wall moving along the periphery of the environment at the target velocity, the wall having a plurality of wall openings that accordingly move at the target velocity, each wall opening having the target size; and implementation of the user incentive includes one or more of (1) increasing the target velocity and (2) increasing a speed at which the target size shrinks during the turn.

* * * * *